(12) United States Patent
Lin et al.

(10) Patent No.: US 7,795,404 B1
(45) Date of Patent: Sep. 14, 2010

(54) HUMAN SOLUBLE NOTCH RECEPTOR LIGANDS

(75) Inventors: Haishan Lin, Castro Valley, CA (US);
Minmei Huang, San Leandro, CA (US);
Lewis T. Williams, Mill Valley, CA (US)

(73) Assignee: Five Prime Therapeutics, Inc., San Francisco, CA (US)

( * ) Notice: Subject to any disclaimer, the term of this patent is extended or adjusted under 35 U.S.C. 154(b) by 157 days.

(21) Appl. No.: 11/985,863

(22) Filed: Nov. 15, 2007

Related U.S. Application Data

(62) Division of application No. 10/913,487, filed on Aug. 9, 2004, now abandoned.

(60) Provisional application No. 60/494,137, filed on Aug. 8, 2003, provisional application No. 60/494,508, filed on Aug. 11, 2003, provisional application No. 60/565,839, filed on Apr. 28, 2004, provisional application No. 60/589,806, filed on Jul. 22, 2004, provisional application No. 60/589,788, filed on Jul. 22, 2004.

(51) Int. Cl.
*C07K 14/435* (2006.01)
(52) U.S. Cl. .............. 530/402; 530/350; 435/69.1; 435/69.7
(58) Field of Classification Search ........... None
See application file for complete search history.

(56) References Cited

U.S. PATENT DOCUMENTS

| | | | |
|---|---|---|---|
| 5,376,060 A * | 12/1994 | Murray | |
| 6,337,387 B1 | 1/2002 | Sakano et al. | |
| 6,656,467 B2 | 12/2003 | Young et al. | |
| 6,664,098 B1 | 12/2003 | Sakano | |
| 7,189,566 B2 | 3/2007 | Botstein et al. | |
| 2004/0142325 A1 * | 7/2004 | Mintz et al. | |

FOREIGN PATENT DOCUMENTS

WO  WO 9401548 A2 *  1/1994

OTHER PUBLICATIONS

Zhou et al. [The extracelllar domain of human delta-like-1 expressed and purified from CHO cells promotes expansion of hematopoietic progenitor cells], Zhongguo Shi Yan Xue Ye Xue Za Zhi, 11(3):222-6, Jun. 2003, translation only.*
Amsen et al., Instruction of Distinct CD4 T Helper Cell Fates by Different Notch Ligands on Antigen-Presenting Cells, *Cell*, 117:515-526 (2004).
Delgado et al., "The Uses and Properties of PEG-Linked Proteins," *Critical Reviews in Therapeutic Drug Carrier Systems*, 9(3,4):249-304 (1992).
Grandbarbe et al., "Delta-Notch signaling controls the generation of neurons/glia from neural stem cells in a stepwise process," *Development*, 130:1391-1402 (2003).
Han et al., "A soluble form of human Delta-like-1 inhibits differentiation of hematopoietic progenitor cells," *Blood*, 95(5):1616-1625 (2000).
Pui et al., "Notch1 Expression in Early Lymphopoiesis Influences B versus T Lineage Determination," *Immunity*, 11(3):299-308 (1999).
Radtke et al., "Deficient T Cell Fate Specification in Mice with an Induced Inactivation of *Notch1*," *Immunity*, 10(5):547-558 (1999).
Schmitt et al., "Induction of T Cell Development from Hematopoietic Progenitor Cells by Delta-like-1 in Vitro," *Immunity*, 17(6):749-756 (2002).
Six et al., "The Notch ligand Delta1 is sequentially cleaved by an ADAM protease and γ-secretase," *Proc. Natl. Acad. Sci. USA*, 100(13):7638-7643 (2003).
Office Action mailed Jun. 15, 2007, in U.S. Appl. No. 10/913,487, filed Aug. 9, 2004.
Preliminary Amendment and Response to Restriction Requirement filed Apr. 19, 2007, in U.S. Appl. No. 10/913,487, filed Aug. 9, 2004.
Restriction Requirement mailed Feb. 14, 2007, in U.S. Appl. No. 10/913,487, filed Aug. 9, 2004.

* cited by examiner

*Primary Examiner*—Gary B. Nickol
*Assistant Examiner*—Claire Kaufman
(74) *Attorney, Agent, or Firm*—Finnegan, Henderson, Farabow, Garrett & Dunner, L.L.P.

(57) ABSTRACT

Novel soluble Notch receptor ligands and polynucleotides encoding such are disclosed, as well as methods for producing and using these novel nucleotides and polypeptides. These novel polypeptides or agonists or antagonists thereto modulate cellular activity, regulate the growth and division of cell, including stem cells, progenitor and precursor cells, are involved in cell fate decisions, and provide prophylactic or therapeutic benefits for treatment of human diseases. Expression systems are provided that facilitate the production, secretion, and purification of these molecules.

14 Claims, 14 Drawing Sheets

FIGURE 3A

Figure 1:
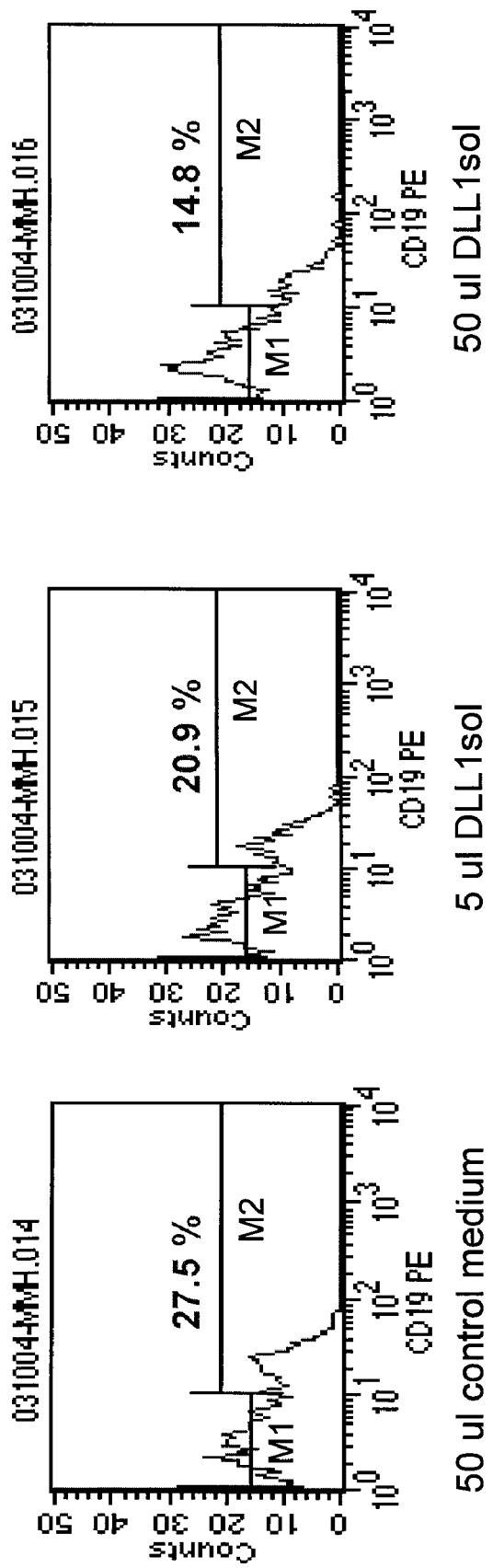

```
Dll1sol            MGSRCALALAVLSALLCQVWSSGVFELKLQEFVNKKGLLGNRNCCRGGAGPPPCACRTFF  60
NP_005609_NM_005618 MGSRCALALAVLSALLCQVWSSGVFELKLQEFVNKKGLLGNRNCCRGGAGPPPCACRTFF  60
                   ************************************************************

Dll1sol            RVCLKHYQASVSPEPPCTYGSAVTPVLGVDSFSLPDGGADSAFSNPIRFPFGFTWPGTF  120
NP_005609_NM_005618 RVCLKHYQASVSPEPPCTYGSAVTPVLGVDSFSLPDGGADSAFSNPIRFPFGFTWPGTF  120
                   ************************************************************

Dll1sol            SLIIEALHTDSPDDLATENPERLISRLATQRHLTVGEEWSQDLHSSGRTDLKYSYRFVCD  180
NP_005609_NM_005618 SLIIEALHTDSPDDLATENPERLISRLATQRHLTVGEEWSQDLHSSGRTDLKYSYRFVCD  180
                   ************************************************************

Dll1sol            EHYYGEGCSVFCRPRDDAFGHFTCGERGEKVCNPGWKGPYCTER------------  224
NP_005609_NM_005618 EHYYGEGCSVFCRPRDDAFGHFTCGERGEKVCNPGWKGPYCTEPICLPGCDEQHGFCDKP  240
                   *******************************************

Dll1sol            ------------------------------------------------------------  224
NP_005609_NM_005618 GECKCRVGWQGRYCDECIRYPGCLHGTCQQPWQCNCQEGWGGLFCNQDLNYCTHHKPCKN  300

Dll1sol            ------------------------------------------------------------  224
NP_005609_NM_005618 GATCTNTGQGSYTCSCRPGYTGATCELGIDECDPSPCKNGGSCTDLENSYSCTCPPGFYG  360

Dll1sol            ------------------------------------------------------------  224
NP_005609_NM_005618 KICELSAMTCADGPCFNGGRCSDSPDGGYSCRCPVGYSGFNCEKKIDYCSSSPCSNGAKC  420

Dll1sol            ------------------------------------------------------------  224
NP_005609_NM_005618 VDLGDAYLCRCQAGFSGRHCDDNVDDCASSPCANGGTCRDGVNDFSCTCPPGYTGRNCSA  480

Dll1sol            ------------------------------------------------------------  224
NP_005609_NM_005618 PVSRCEHAPCHNGATCHQRGHGHYVCECARSYGGPNCQFLLPELPPGPAVVDLTEKLEGQG  540
```

FIGURE 3B

```
Dlllsol              ------------------------------------------------  ---  224
NP_005609_NM_005618  GPFPWVAVCAGVILVLMLLLGCAAVVVCVRLRLQKHRPPADPCRGETETMNNLANCQREK  600

Dlllsol              ------------------------------------------------  ---  224
NP_005609_NM_005618  DISVSIIGATQIKNTNKKADFHGDHSADKNGFKARYPAVDYNLVQDLKGDDTAVRDAHSK  660

Dlllsol              ------------------------------------------------  ---  224
NP_005609_NM_005618  RDTKCQPQGSSGEEKGTPTTLRGGEASERKRPDSGCSTSKDTKYQSVYVISEEKDECVIA  720

Dlllsol              ---  224
NP_005609_NM_005618  TEV  723
```

FIGURE 4A

```
Dll1sol           ------------------------------------------------------------       0
NP_005609_NM_005618  AAACCGGAAACGGGGCCCAACTTCTGGGCCTGGAGAAGGGAAACGAAGTCCCCCCGGTT      60
Dll1sol_3pv1      ------------------------------------------------------------       0

Dll1sol           ------------------------------------------------------------       0
NP_005609_NM_005618  TCCCGAGGTTGCCTTTCCTCGGGCATCCTTGGTTTCGGCGGGACTTCGCAGGGCGGATAT     120
Dll1sol_3pv1      ------------------------------------------------------------       0

Dll1sol           ------------------------------------------------------------       0
NP_005609_NM_005618  AAAGAACGGCGCCTTTGGGAAGAGGCGGAGACCGGCTTTAAAGAAAGAAGTCTTGGTCCT     180
Dll1sol_3pv1      ------------------------------------------------------------       0

Dll1sol           ------------------------------------------------------------       0
NP_005609_NM_005618  GCGGCTTGGGCGAGGCAAGGGCGGAGGCAAGGCGCGCTTTCTGCCGACGCTCCCCGTGGCCC    240
Dll1sol_3pv1      ------------------------------------------------------------       0

Dll1sol           ------------------------------------------------------------       0
NP_005609_NM_005618  TACGATCCCCCGCGCGTCCGCGCCGTCGTTCTAAGGAGAGAAGTGGGGCCCCCCAGGCTCG    300
Dll1sol_3pv1      ------------------------------------------------------------       0

Dll1sol           ------------------------------------ATGGGCAGTCGGTGCGCGCTCTCGGCC     42
NP_005609_NM_005618  CGCGTGGAGCGAAGCAGCATGGGCAGTCGGTGCGCGGTGCGCGCTCTCGGCC    360
Dll1sol_3pv1      ------------------------------------------------------------       0
```

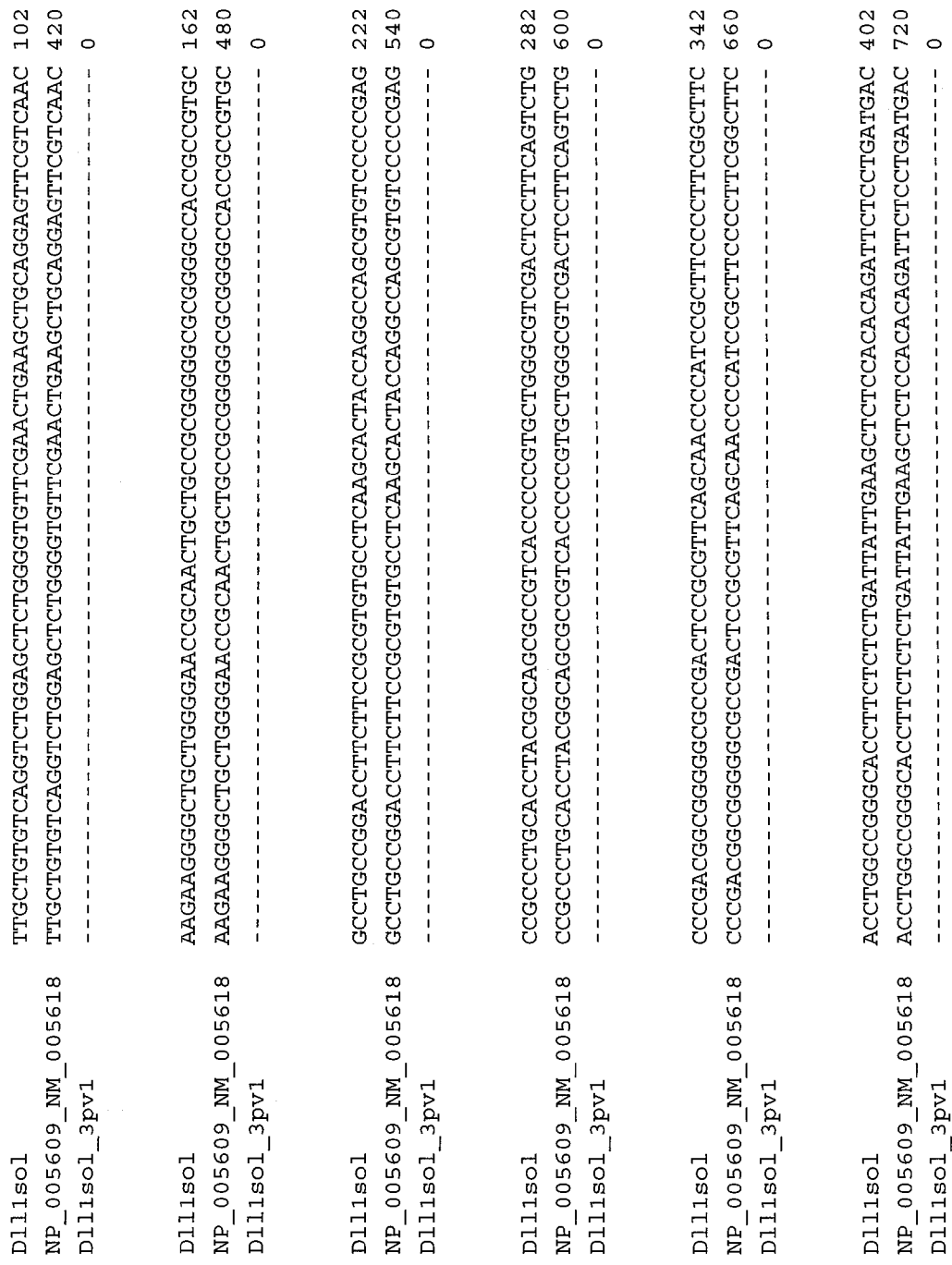

FIGURE 4D

```
Dlllsol             AGGCGCAGGACACCCGCGCCGGCTCCCATTGGCGGAAGGGCGATCTGCCTGCCTGGATGTG    822
NP_005609_NM_005618 ------------------------------------------------CGATCTGCCTGCCTGGATGTG   1009
Dlllsol_3pv1        ------------------------------------------------------------      0

Dlllsol             ATGAGCAGCATGGATTTTGTGACAAACCAGGGGAATGCAAGTGCAGAGTGGGCTGGCAGG    882
NP_005609_NM_005618 ATGAGCAGCATGGATTTTGTGACAAACCAGGGGAATGCAAGTGCAGAGTGGGCTGGCAGG   1069
Dlllsol_3pv1        ------------------------------------------------------------      0

Dlllsol             GCCGGTACTGTGACGAGTGTATCCGCTATCCAGGCTGTCTCCATGGCACCTGCCAGCAGC    942
NP_005609_NM_005618 GCCGGTACTGTGACGAGTGTATCCGCTATCCAGGCTGTCTCCATGGCACCTGCCAGCAGC   1129
Dlllsol_3pv1        ------------------------------------------------------------      0

Dlllsol             CCTGGCAGTGCAACTGCCAGGAAGGCTGGGGGGCCTTTTCTGCAACCAGGACCTGAACT   1002
NP_005609_NM_005618 CCTGGCAGTGCAACTGCCAGGAAGGCTGGGGGGCCTTTTCTGCAACCAGGACCTGAACT   1189
Dlllsol_3pv1        ------------------------------------------------------------      0

Dlllsol             ACTGCACACACACCATAAGCCCTGCAAGAATGGAGCCACCTGCACCAACACGGGCCAGGGGA   1062
NP_005609_NM_005618 ACTGCACACACACCATAAGCCCTGCAAGAATGGAGCCACCTGCACCAACACGGGCCAGGGGA   1249
Dlllsol_3pv1        ------------------------------------------------------------      0

Dlllsol             GCTACACTTGCTCTTGCCGGCCTGGGTACACAGGTGCCACCTGCGAGCTGGGGATTGACG   1122
NP_005609_NM_005618 GCTACACTTGCTCTTGCCGGCCTGGGTACACAGGTGCCACCTGCGAGCTGGGGATTGACG   1309
Dlllsol_3pv1        ------------------------------------------------------------      0
```

FIGURE 4E

```
Dll1sol              AGTGTGACCCCAGCCCTTGTAAGAACGGAGGGAGCTGCACGGATCTCGAGAACAGCTACT 1182
NP_005609_NM_005618  AGTGTGACCCCAGCCCTTGTAAGAACGGAGGGAGCTGCACGGATCTCGAGAACAGCTACT 1369
Dll1sol_3pv1         ------------------------------------------------------------ 0

Dll1sol              CCTGTACCTGCCCACCCGGCTTCTACGGCAAAATCTGTGAATTGAGTGCCATGACCTGTG 1242
NP_005609_NM_005618  CCTGTACCTGCCCACCCGGCTTCTACGGCAAAATCTGTGAATTGAGTGCCATGACCTGTG 1429
Dll1sol_3pv1         ------------------------------------------------------------ 0

Dll1sol              CGGACGGCCCTGCTTTAACGGGGTCGGTGCTCAGACAGCCCCGATGGAGGGTACAGCT 1302
NP_005609_NM_005618  CGGACGGCCCTTGCTTTAACGGGGTCGGTGCTCAGACAGCCCCGATGGAGGGTACAGCT 1489
Dll1sol_3pv1         ------------------------------------------------------------ 0

Dll1sol              GCCGCTGCCCCCGTGGGCTACTCCGGCTTCAACTGTGAGAAGAAAATTGACTACTGCAGCT 1362
NP_005609_NM_005618  GCCGCTGCCCCCGTGGGCTACTCCGGCTTCAACTGTGAGAAGAAAATTGACTACTGCAGCT 1549
Dll1sol_3pv1         ------------------------------------------------------------ 0

Dll1sol              CTTCACCCTGTTCTAATGGTGCCAAGTGTGTGGACCTCGGTGATGCCTACCTGTGCCGCT 1422
NP_005609_NM_005618  CTTCACCCTGTTCTAATGGTGCCAAGTGTGTGGACCTCGGTGATGCCTACCTGTGCCGCT 1609
Dll1sol_3pv1         ------------------------------------------------------------ 0

Dll1sol              GCCAGGCCGGCTTCTCGGGGAGGCACTGTGACGACAACGTGGACGACTGCGCCTCCTCCC 1482
NP_005609_NM_005618  GCCAGGCCGGCTTCTCGGGGAGGCACTGTGACGACAACGTGGACGACTGCGCCTCCTCCC 1669
Dll1sol_3pv1         ------------------------------------------------------------ 0
```

FIGURE 4G

```
Dll1sol           TGAGGCTGCAGAAGCACCGGCCCCCAGCCGACCCTGCCGGGGAGACGGAGACCATGA 1902
NP_005609_NM_005618 TGAGGCTGCAGAAGCACCGGCCCCCAGCCGACCCTGCCGGGGAGACGGAGACCATGA 2089
Dll1sol_3pv1      ---------------------------------------------------------    0

Dll1sol           ACAACCTGGCCAACTGCCAGCGTGAGAAGGACATCTCAGTCAGCATCATCGGGCCACGC 1962
NP_005609_NM_005618 ACAACCTGGCCAACTGCCAGCGTGAGAAGGACATCTCAGTCAGCATCATCGGGCCACGC 2149
Dll1sol_3pv1      ---------------------------------------------------------    0

Dll1sol           AGATCAAGAACACCAACAAGAAGGCGGACTTCCACGGGGACCACAGCGCCGACAAGAATG 2022
NP_005609_NM_005618 AGATCAAGAACACCAACAAGAAGGCGGACTTCCACGGGGACCACAGCGCCGACAAGAATG 2209
Dll1sol_3pv1      ---------------------------------------------------------    0

Dll1sol           GCTTCAAGGCCCGCTACCCAGCGGTGGACTATAACCTCGTGCAGGACCTCAAGGGTGACG 2082
NP_005609_NM_005618 GCTTCAAGGCCCGCTACCCAGCGGTGGACTATAACCTCGTGCAGGACCTCAAGGGTGACG 2269
Dll1sol_3pv1      ---------------------------------------------------------    0

Dll1sol           ACACCGCCGTCAGGGACGCGCACAGCAAGCGTGACACCAAGTGCCAGCCCCAGGGCTCCT 2142
NP_005609_NM_005618 ACACCGCCGTCAGGGACGCGCACAGCAAGCGTGACACCAAGTGCCAGCCCCAGGGCTCCT 2329
Dll1sol_3pv1      ---------------------------------------------------------    0

Dll1sol           CAGGGGAGGAGAAGGGGACCCCGACCACTCAGGGGTGGAGAAGCATCTGAAAGAAAAA 2202
NP_005609_NM_005618 CAGGGGAGGAGAAGGGGACCCCGACCACTCAGGGGTGGAGAAGCATCTGAAAGAAAAA 2389
Dll1sol_3pv1      ---------------------------------------------------------    0
```

FIGURE 4H

```
Dl11sol         ------------------------------------------------------------  2262
NP_005609_NM_005618  GGCCGGACTCGGGCTGTTCAACTTCAAAAGACACCAAGTACCAGTCGGTGTACGTCATAT  2449
Dl11sol_3pv1    ------------------------------------------------------------  0

Dl11sol         ------------------------------------------------------------  2303
NP_005609_NM_005618  CCGAGGAGAAGGATGAGTGCGTCATAGCAACTGAGGTGTAA-------------------  2509
Dl11sol_3pv1    ------------------------------------NNNNNNNNNNNNNNNNNNNNNNNN  0

Dl11sol         ------------------------------------------------------------  2303
NP_005609_NM_005618  GACTCCCGTTTCTCTTAAAAATAAGTAAAATTCCAAGGATATATGCCCCAACGAATGCTGC  2569
Dl11sol_3pv1    NNNNNNNNNNNNNNNNNNNNNNNNNNNNNNNNNNNNNNNNNNNNNNNNNNNNNNNNNNNN  0

Dl11sol         ------------------------------------------------------------  2303
NP_005609_NM_005618  TGAAGAGGAGGAGGGAGGCCTCGTGGACTGCTGCTGAGAAACCGAGTTCAGACCGAGCAGGTT  2629
Dl11sol_3pv1    NNNNGAGGAGGAGGGAGGCCTCGTGGACTGCTGCTGAGAAACCGAGTTCAGACCGAGCAGGTT  56

Dl11sol         ------------------------------------------------------------  2303
NP_005609_NM_005618  CTCCTCCTGAGGTCCTCCTCGACGCTGCCGACAGCCTGTCGCGGCCGCCCTGCGGCAC     2689
Dl11sol_3pv1    CTCCTCCTGAGGTCCTCCTCGACGCTGCCGACAGCCTGTCGCGGCCCCGGCCTGCGGCAC   116

Dl11sol         ------------------------------------------------------------  2303
NP_005609_NM_005618  TGCCTTCCGTGACGTCGCCGTTGCACTATGACAGTTGCTCTTAAGAGAATATATATTTA   2749
Dl11sol_3pv1    TGCCTTCCGTGACGTCGCCGTTGCACTATGGACAGTTGCTCTTAAGAGAATATATATTTA  176
```

FIGURE 4I

```
Dll1sol          ------------------------------------------------------------   2303
NP_005609_NM_005618  AATGGGTGAACTGAATTACGCCTAAGAAGCATGCACTGCCTGAGTGTATATTTGGATTC   2809
Dll1sol_3pv1     AATGGGTGAACTGAATTACGCATAAGAAGCATGCACTGCCTGAGTGTATATTTGGATTC   236

Dll1sol          ------------------------------------------------------------   2303
NP_005609_NM_005618  TTATGAGCCAGTCTCTTTTCTTGAATTAGAAACACAAACACTGCCTTTATTGTCCTTTTGA   2869
Dll1sol_3pv1     TTATGAGCCAGTCTCTTTTCTTGAATTAGAAACACAAACACTGCCTTTATTGTCCTTTTGA   296

Dll1sol          ------------------------------------------------------------   2303
NP_005609_NM_005618  TACGAAGATGTGCTTTTTCTAGATGGAAAAGATGTGTTATTTTTGGATTTGTAAAAA   2929
Dll1sol_3pv1     TACGAAGATGTGCTTTTTCTAGATGGAAAAGATGTGTTATTTTTTGGATTTGTAAAAA   356

Dll1sol          ------------------------------------------------------------   2303
NP_005609_NM_005618  TATTTTTCATGATATCTGTAAAGCTTGAGTATTTTGTGATGTTCGTTTTTTATAATTTAA   2989
Dll1sol_3pv1     TATTTTTCATGATATCTGTAAAGCTTGAGTATTTTGTGATGTTCGTTTTTTATAATTTAA   416

Dll1sol          ------------------------------------------------------------   2303
NP_005609_NM_005618  ATTTTGGTAAATATGTACAAAGGCACTTCGGGTCTATGTGACTATATTTTTTGTATATA   3049
Dll1sol_3pv1     ATTTTGGTAAATATGTACAAAGGCACTTCGGGTCTATGTGACTATATTTTTTGTATATA   476

Dll1sol          ------------------------------------------------------------   2303
NP_005609_NM_005618  AATGTATTTATGGAATATTGTGCCAAATGTTATTTGAGTTTTTTACTGTTTTGTTAATGAA   3109
Dll1sol_3pv1     AATGTATTTATGGAATATTGTGCAAATGTTATTTGAGTTTTTTACTGTTTTGTTAATGAA   536
```

FIGURE 4J

```
Dl11sol                   ------------------------------------------------------------  2303
NP_005609_NM_005618       GAAATTCCTTTTTAAAAATATTTTC-CAAAATAAATTTATGA-GGAATTC-----------  3158
Dl11sol_3pv1              GAAATTCCTTTTTTAAAAATATTTTTCGCAAAATAAATTTTATGAATGACAAAAAAAAAAA  596

Dl11sol                   ----- 2303
NP_005609_NM_005618       ----- 3158
Dl11sol_3pv1              AAAAA 601
```

HUMAN SOLUBLE NOTCH RECEPTOR LIGANDS

PRIORITY CLAIM

This application is a divisional of U.S. patent application Ser. No. 10/913,487, filed Aug. 9, 2004 now abandoned, which claims the benefit of U.S. Provisional 60/494,137, Human Soluble Delta-Like-1 Protein, filed in the U.S. Patent and Trademark Office Aug. 8, 2003, and U.S. Provisional 60/494,508, Human Soluble Notch Receptor Ligands, filed in the U.S. Patent and Trademark Office Aug. 11, 2003, the disclosures of which are incorporated in their entireties. This application also incorporates U.S. Provisional Application 60/565,839, Reporter System for Detecting Signal Pathway Activation, filed in the U.S. Patent and Trademark Office Apr. 28, 2004, U.S. Provisional Application 60/589,806, Inhibitory RNA Library, filed in the U.S. Patent and Trademark Office Jul. 22, 2004, and U.S. Provisional Application 60/589,788, Fusion Polypeptides of Human Fetuin and Therapeutically Active Polypeptides, filed in the U.S. Patent and Trademark Office Jul. 22, 2004, in their entireties.

FIELD OF THE INVENTION

The present invention relates to novel human polynucleotides encoding soluble Notch receptor ligands, including, for example, human, mouse, and rat Delta-like-1 (DLL1sol), Delta-like-3 (DLL3sol), Delta-like-4 (DLL4sol), Jagged 1 (Jagged1sol), and Jagged 2 (Jagged2sol). The invention also relates to the encoded polypeptides and compositions containing these polynucleotides and polypeptides. The invention specifically relates to the provision of naturally occurring splice variants of DLL1. The invention further relates to methods of using these polynucleotides and polypeptides for treating diseases affected by the human Notch signaling pathway including, for example, cancer, disorders of the immune system, inflammatory disease, AIDS, neuronal disorders, diseases related to the regulation of T cell development, and hematopoiesis, as well as lung, pancreas, and neural development.

BACKGROUND OF THE INVENTION

The Notch signaling pathway has been implicated in cell fate decisions mediated by cell-cell interactions via the Notch receptor and the Notch ligands Delta and Serrate/Jagged, which were initially discovered in *Drosophila*, for example, as described by Six, et al., 2003; and Han and Moore, 2000. Notch signaling has been found to be conserved in mammalian systems, and has been implicated in a number of important cell functions, as described in, for example, de la Pompa, et al., 1997; Apelqvist, et al., 1999; Singh, et al., 2000; Post, et al., 2000; Tezuka, et al., 2002; and Grandbarbe, et al., 2003.

Six, E. et al. (2003) have described a murine ligand Delta1 (Dll1) that was cleaved at a cleavage site 10 aa N-terminal to the TM domain, between His-535 and Met-536. Han, et al., 2000 isolated a cDNA clone encoding a human homolog of the mouse Delta-like-1 gene, designated human Delta-like-1 (hDll1). They artificially created a soluble form, hDll1$^{NDSL}$, which contained the DSL domain and its adjacent N-terminal 50 amino acids (aa 127-225), and expressed and purified this molecule from bacteria as a glutathione S-transferase (GST) fusion protein. No naturally occurring soluble human Delta-like-1 protein has to date been identified or isolated.

SUMMARY OF THE INVENTION

The inventors have herein identified a class of novel soluble Notch receptor ligands. These soluble Notch receptor ligands are naturally-occurring splice variants which, in contrast to the full length molecules, do not contain any transmembrane domains. The Notch receptor ligands herein each include a DSL domain and, optionally, its adjacent C-terminal one, two, three, or four amino acid residues, with or without the substitution of arginine (R) for the last C-terminal amino acid residue.

Thus, for example, the invention includes the polynucleotide of SEQ ID NO: 1 and fragments thereof; polynucleotides encoding the polypeptides of SEQ ID NO: 3, SEQ ID NO: 4, SEQ ID NO: 5, and SEQ ID NO: 6, and fragments thereof; and the polynucleotides of SEQ ID NO: 8 and SEQ ID NO: 11, and fragments thereof.

The invention includes a soluble Notch receptor ligand comprising a first polypeptide comprising a DSL domain and an additional one, two, three, or four amino acid residues adjacent to the DSL domain at its C-terminus, wherein the terminal amino acid residue is an arginine (R).

This soluble Notch receptor ligand of claim 1, can have fewer amino acids than full-length human Notch receptor ligand DLL1 and does not include fragments consisting of amino acid residues 127-225 of human DLL1. It can comprise any amino acid sequence chosen from SEQ. ID. NO: 3 to SEQ ID NO: 6, inclusive, and/or one or more active fragments thereof.

The invention also includes a soluble Notch receptor ligand comprising a polypeptide encoded by a nucleotide sequence of SEQ ID NO: 1 or SEQ. ID. NO: 8, and biologically active fragments thereof. This nucleotide sequence can be optimized for expression in a system chosen from a cell-free expression system, an *E. coli* expression system, a yeast expression system, an insect expression system, and a mammalian cell expression system.

The soluble Notch receptor ligand of the invention can further comprise a second molecule. This second molecule can facilitate production, secretion, and/or purification. In some embodiments it can confer a longer half-life to the ligand when administered to an animal. Examples of the second molecule of the invention include, but are not limited to polyethylene glycol (PEG), human serum albumin (HAS), fetuin, or a fragment of any of these.

The soluble Notch receptor ligand of the invention may regulate lymphocyte differentiation or proliferation. It may suppress B lymphocyte differentiation or proliferation. It may promote T lymphocyte differentiation or proliferation.

The invention provides an isolated nucleic acid molecule comprising a nucleotide sequence encoding a sense or antisense sequence of the soluble Notch receptor ligand of the invention. This nucleic acid molecule can be a DNA, RNA, DNA/RNA hybrid, or a peptide nucleic acid molecule. The isolated nucleic acid molecule of can be a cDNA, a cRNA, an RNAi, a siRNA, or a ribozyme.

The invention also provides a vector comprising a nucleic acid molecule of the invention and a promoter. It provides a recombinant host cell comprising one or more of such a vector, a nucleic acid molecule of the invention, and/or a Notch receptor ligand of the invention, or one or more fragments of any of these.

Further, for example, the fragments of the present invention include soluble Notch receptor ligands each containing a DSL domain and optionally, its adjacent C-terminal one, two, three, and/or four amino acid residues, with or without the substitution of R for the last amino acid residue; provided however, that if such fragment contains amino acid residues 127 to 225 of DLL1 (SEQ ID NO: 7), the last amino acid residue of such fragment is an R. Additionally, the fragments of the present invention include amino acid residues of SEQ ID NO: 3, SEQ ID NO: 4, SEQ ID NO: 5, and SEQ ID NO:6, and polynucleotides encoding such. The fragments of the present invention further include those described above plus modifications thereof in which the last amino acid residue is substituted with R, or an additional amino acid residue, R, is added at its C-terminus. The fragments of the present invention include fragments of Notch ligand receptors containing only the DSL domains, in which the last amino acid residue is substituted with amino acid residue R, or to which amino acid R has been added to its C-terminus. Fragments of the invention can be biologically active.

Polypeptides of the invention can be optimized for expression in a cell-free expression system, an *E. coli* expression system, a yeast expression system, an insect expression system, and/or a mammalian cell expression system.

The invention also provides for a method of transfecting a host cell by providing a vector comprising a sequence selected from SEQ ID NO: 1, SEQ ID NO: 8, a complement of such, a degenerate sequence of such, and a biologically active fragment of such; at least one promoter that drives the expression of the vector; and allowing a host cell to come into contact with the vector to form a transfected host cell. The host cell can be a eukaryotic cell. In practicing this method, over-expressing the vector can result in an increase in multilineage cells, progenitor cells, precursor cells, and/or stem cells. The promoter may be naturally contiguous to the nucleic acid molecule or it may not be naturally contiguous to the nucleic acid molecule. The promoter can be inducible, conditionally-active, constitutive, and/or tissue-specific.

The invention further provides a method of making a polypeptide by providing a translation system in a host cell transfected with SEQ ID NO: 1 or SEQ ID NO: 8, a complement, a degenerate sequence, and/or a biologically active fragment of these polynucleotides; culturing the transfected host cell to produce the polypeptide; and obtaining the polypeptide from the culture. The translation system can be an in vitro system. The host cell can be a prokaryotic cell or a eukaryotic cell. If the host cell is a prokaryotic cell, it may be an *E. coli* cell. If the host cell is a eukaryotic cell, it may be a human cell, a non-human mammalian cell, an insect cell, a fish cell, a plant cell, or a fungal cell. If the host cell is a fungal cell, it may comprise a yeast cell.

The invention further provides a method of making a polypeptide by providing a sequence of SEQ ID NO: 1 or SEQ ID NO: 8, a complement, a degenerate sequence, and/or a biologically active fragment of these polynucleotides; contacting the nucleic acid molecule with a translation system to allow polypeptide synthesis; and obtaining the polypeptide from the synthesis. The translation system can be a cell-free, in vitro system, for example, a wheat germ lysate system, a rabbit reticulocyte system, an *E. coli* lysate system, or a frog oocyte system.

The invention provides a method of producing a recombinant host cell comprising a Notch receptor ligand by providing a vector comprising one or more of SEQ ID NO:1 and SEQ ID NO:8, a complement, a degenerate sequence, and a biologically active fragment of these polynucleotides; and at least one promoter that drives the expression of the vector; and allowing a host cell to come into contact with the vector to form a transfected host cell.

The invention provides a method of making a polypeptide by providing a translation system in a host cell transfected with a nucleotide molecule chosen from one or more of SEQ ID NO: 1 and SEQ ID NO: 8, a complement, a degenerate sequence, and/or a biologically active fragment of these polynucleotides, and culturing the transfected host cell to produce the polypeptide.

The invention also provides a method of making a polypeptide by providing a nucleic acid molecule chosen from one or more of SEQ ID NO: 1 and SEQ ID NO: 8, a complement, a degenerate sequence, and/or a biologically active fragment of these polynucleotides and contacting the nucleic acid molecule with a translation system to produce the polypeptide. This method includes a translation system that is a cell-free, in vitro system.

The invention provides a method of determining the presence of at least one polynucleotide of SEQ ID NO: 1 and SEQ ID NO: 8, a complement, a degenerate sequence, and/or a biologically active fragment thereof; or the complement of any of these, by providing a complement to the nucleic acid molecule or providing a complement to the complement of the nucleic acid molecule; allowing the molecules to interact; and determining whether interaction has occurred.

The invention provides a method of determining the presence of an antibody to at least one polypeptide chosen from SEQ ID NO: 3 to SEQ ID NO: 6, inclusive, or a biologically active fragment thereof, by providing the polypeptide; allowing the polypeptide to interact with any specific antibody in the sample; and determining whether interaction has occurred.

The invention also provides a method of regulating the growth or differentiation of a target cell by providing at least one polypeptide chosen from SEQ ID NO: 3 to SEQ ID NO: 6, inclusive, or a biologically active fragment any of these, and contacting the target cell with the polypeptide, whereby the growth or differentiation of the target cell is regulated. The target cell can be a stem cell, a bone marrow cell, a neuronal cell, a hematopoietic cell, a muscle cell, a thymic cell, a spleen cell, and/or a cancer cell. Furthermore, the target cell can be an embryonic stem cell, a committed stem cell, a hematopoeitic stem cell, a myogenic stem cell, a cardiac muscle stem cell, a vascular stem cell, a neural stem cell, a mesenchymal stem cell, a liver stem cell, a pancreatic stem cell, a skin stem cell, a kidney stem cell, a lung stem cell, a gastrointestinal stem cell, a spleen stem cell, a breast stem cell, a prostate stem cell, a testicular stem cell, and/or an ovarian stem cell. The pancreatic stem cell may be a pancreatic islet stem cell.

The method of regulating growth includes regulating either growth promotion or growth inhibition. When this method regulates growth promotion, the regulation of the invention can induce the cell to produce a replica of itself. The regulation of the invention can also induce the cell to differentiate into lineage-restricted committed progenitor cells.

The invention further provides a method of modulating cellular function, by providing at least one nucleic acid or polypeptide of SEQ ID NO: 1, SEQ ID NO: 3 to SEQ ID NO: 6 inclusive, SEQ ID NO: 8, a complement, a degenerate sequence, and/or a biologically active fragment thereof; and administering the nucleic acid or polypeptide to a patient, in an manner sufficient to modulate cellular function.

The invention yet further provides a method of prophylaxis or therapeutic treatment of a patient in need of such treatment, by providing at least one nucleic acid or polypeptide chosen from SEQ ID NO: 1, SEQ ID NO: 3 to SEQ ID NO: 6 inclusive, SEQ ID NO: 8, or a complement, a degenerate sequence, and/or a biologically active fragment thereof; and administering the nucleic acid or polypeptide to the patient. The prophylactic or therapeutic polypeptide can be a naked protein, a chemically modified protein, and/or a fusion protein.

The invention provides a method of treating a patient by stimulating the production of hematopoeitic cells, for example, lymphocytic cells, or other precursor cells, progenitor cells, or stem cells in a patient in need of such treatment by providing a composition comprising at least one polypeptide of SEQ ID NO: 3 to SEQ ID NO: 6 inclusive, or a biologically active fragment thereof; and contacting these cells with a therapeutically effective amount of the polypeptide. The method can be practiced by contacting the cells of the patient with the polypeptide by administering a composition comprising the polypeptide to the patient. This composition may further comprise a pharmaceutically acceptable carrier or a buffer. Contacting the cells of the patient with the polypeptide can, e.g., comprise contacting the cells ex vivo to produce treated cells. The method further comprises administering the treated cells to the patient. This method can be practiced after the patient has undergone chemotherapy and/or radiotherapy. This treatment method can be practiced with a cell free polypeptide composition. Alternatively, it can be practiced with a polypeptide composition comprising a plurality of cells that produce the polypeptide. In this method, the polypeptide can be mutated to optimize its activity. It can also be a fusion polypeptide.

The invention also provides a method of gene therapy treatment of a patient in need of such treatment, by providing at least one nucleotide of SEQ ID NO: 1, SEQ ID NO: 2, SEQ ID NO: 8, or SEQ ID NO:9, a complement, a degenerate sequence, and/or a biologically active fragment thereof; and administering the polynucleotide to the patient.

The invention further provides a method of modulating cell growth, differentiation, function, or activity in a subject in need of such modulation, by administering a composition comprising a therapeutically effective amount of a modulator selected from a polypeptide of SEQ. ID. NO:3 to SEQ ID NO: 6 inclusive, a polypeptide encoded by SEQ. ID. NO: 1 or SEQ ID NO: 8, an agonist, and an antagonist thereof. The modulated cell function or activity can include, e.g., a function or activity associated with cancer, disorders of the immune system, inflammatory disease, AIDS, neuronal disorders, diseases related to T cell development, diseases related to hematopoiesis, and/or diseases related to lung, pancreas, or neural development. The antagonist can be, e.g., an antibody.

BRIEF DESCRIPTIONS OF THE TABLES AND FIGURES

Table 1: Structural Characteristics of DLL1sol Compared to DLL1. Table 1 provides information characteristic of Dll1sol (SEQ ID NO: 3) and of the previously described DLL1 NP_005609:NM_005618, the latter of which is a single transmembrane type 1 membrane protein (Classification). Table 1 provides the predicted length of the polypeptide as the number of amino acid residues (Pred. Protein Length). Table 1 also specifies the result of an algorithm that predicts whether a sequence is secreted (Tree vote). This algorithm is constructed on the basis of a number of attributes that include hydrophobicity, two-dimensional structure, prediction of signal sequence cleavage site, and other parameters. A high Tree vote score indicates that the polypeptide is more likely to be secreted; the scale ranges from 0 to 1. The signal peptide coordinates (Signal Peptide Coords.) are shown. Coordinates listed in the tables herein are shown in terms of their amino acid residues beginning with "1" at the N-terminus of the polypeptide. The "Mature Protein Coords." refer to the coordinates of the amino acid residues of the mature polypeptide after cleavage of the signal peptide. In instances where the mature protein start residue overlaps the signal peptide end residue, some of the amino acid residues may be cleaved off such that the mature protein does not start at the next amino acid residue from the signal peptides, resulting in the alternative mature protein coordinates. Table 1 also specifies the coordinates of alternative forms of the mature protein (Alternate Mature Protein Coords.) and alternative forms of the signal peptide (Alternate Signal Peptide Coords.).

Table 1 also provides the coordinates of hydrophobic regions of the polypeptides (Hydrophobicity Coords.), the transmembrane regions of the polypeptides (TM Coords.), if any, and the number of transmembrane domains (TM). The non-transmembrane coordinates (non-TM Coords) refer to the amino acids that are not transmembrane; these can include extracellular, cytoplasmic, and luminal sequences. The presence of a TM domain in a secreted protein is consistent with an extracellular domain that is cleaved from the protein.

Table 2: Pfam Coordinates. Table 2 provides the internal reference (FP ID) for DLL1sol and NP_005609: NM_00518, as well as the coordinates of the DSL and EGF domains of each. The "Pfam" system is an organization of protein sequence classification and analysis, based on conserved protein domains; it can be publicly accessed in a number of ways, for example, at http://pfam.wustl.edu. Protein domains are portions of proteins that have a tertiary structure and sometimes have enzymatic or binding activities; multiple domains can be connected by flexible polypeptide regions with a protein. Pfam domains can be connected by flexible polypeptide regions within a protein. Pfam domains can comprise the N-terminus or the C-terminus of a protein, or can be situated at any point in between. The Pfam system identifies protein families based on these domains and provides an annotated, searchable database that classifies proteins into families (Bateman et al., 2002). DLL1sol comprises a DSL domain. NP_005609:NM_005618 comprises a DSL and six EGF Pfam domains. DSL domains are comprised of ligands of the Delta/Serrate/lag2 (DSL) family. These domains bind to members of the Notch family of receptors to mediate intercellular interactions that regulate development and differentiation. EGF domains are comprised of 30-40 amino acids with cysteine-mediated disulfide bonds. EGF domains are commonly found in secreted proteins and in the extracellular domains of membrane proteins.

Table 3 describes the characteristics of the human polypeptide in the NCBI database with the greatest degree of similarity to DLL1sol and to NP_005609:NM_005618 (Source ID). These polypeptides, i.e., top human hits, are described by their NCBI accession numbers (Top Human Hit Accession ID) and by the NCBI's annotation of the top human hit (Top Human Hit Annotation). The number of amino acids in the top human hit is specified (Top Human Hit Length). The length of the match between the polypeptide and the top human hit is specified (Number of Matches). The percent identity between the Source ID and top human hit with respect to the length of the polypeptide is specified (% ID over Query Length). Finally, the percent identity between the Source ID and the top human hit with respect to the length of the top human hit is specified (% ID over Human Hit Length).

FIG. 1: In vitro B Cell Development Assay. Human bone marrow CD34$^+$ hematopoeitic stem cells (HSC) were co-cultured for 7 days with OP9 stromal cells in the absence or presence of human DLL1sol protein, as described in Example 2. B cell-specific markers were analyzed by FACS analysis. Cultures treated with 50 ul control media comprised 27.5%

CD19+ B cells, cultures treated with 5 ul media with DLL1sol comprised 20.9% CD19+ B cells, and cultures treated with 50 ul media with DLL1sol comprised 14.8% CD19+ B cells.

Figure 2:
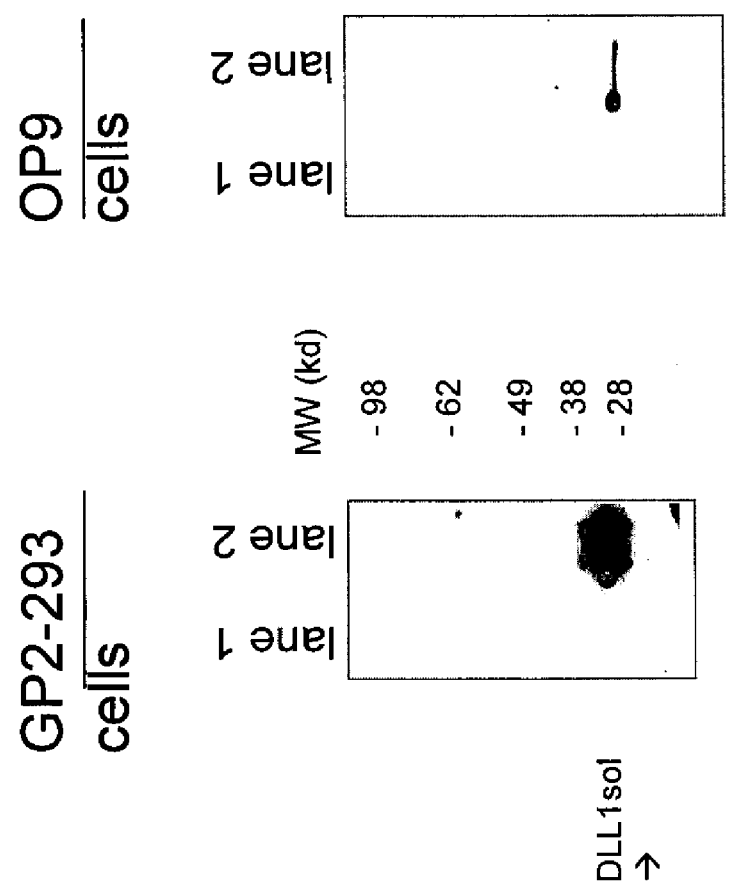

FIG. 2: In Vitro T Cell Development Assay. Human bone marrow CD34+ HSC were co-cultured for two weeks with OP9 stromal cells stably infected with a retroviral vector encoding the DLL1sol protein, as described in Example 3. DLL1sol protein is indicated by the arrow. It was not expressed in control cells (lane 1), but was expressed in and produced by both the GP2-293 cells (lane 2) and OP9 cells (lane 2) in a soluble form. MW indicates the polypeptide molecular weight markers, expressed in kilodaltons (kd).

FIG. 3: Amino acid sequence alignment of DLL1sol (SEQ ID NO:3), compared to the DLL1 sequence NP_005609_NM_005618 (SEQ ID NO:7) obtained from the NCBI public database. The asterisks (*) indicate shared amino acid residues. The alignment was generated using Clustal Format for T-COFFEE Version_1.37, CPU=0.00 sec, score=100, Nseq=2, and Len=723.

Figure 4C:
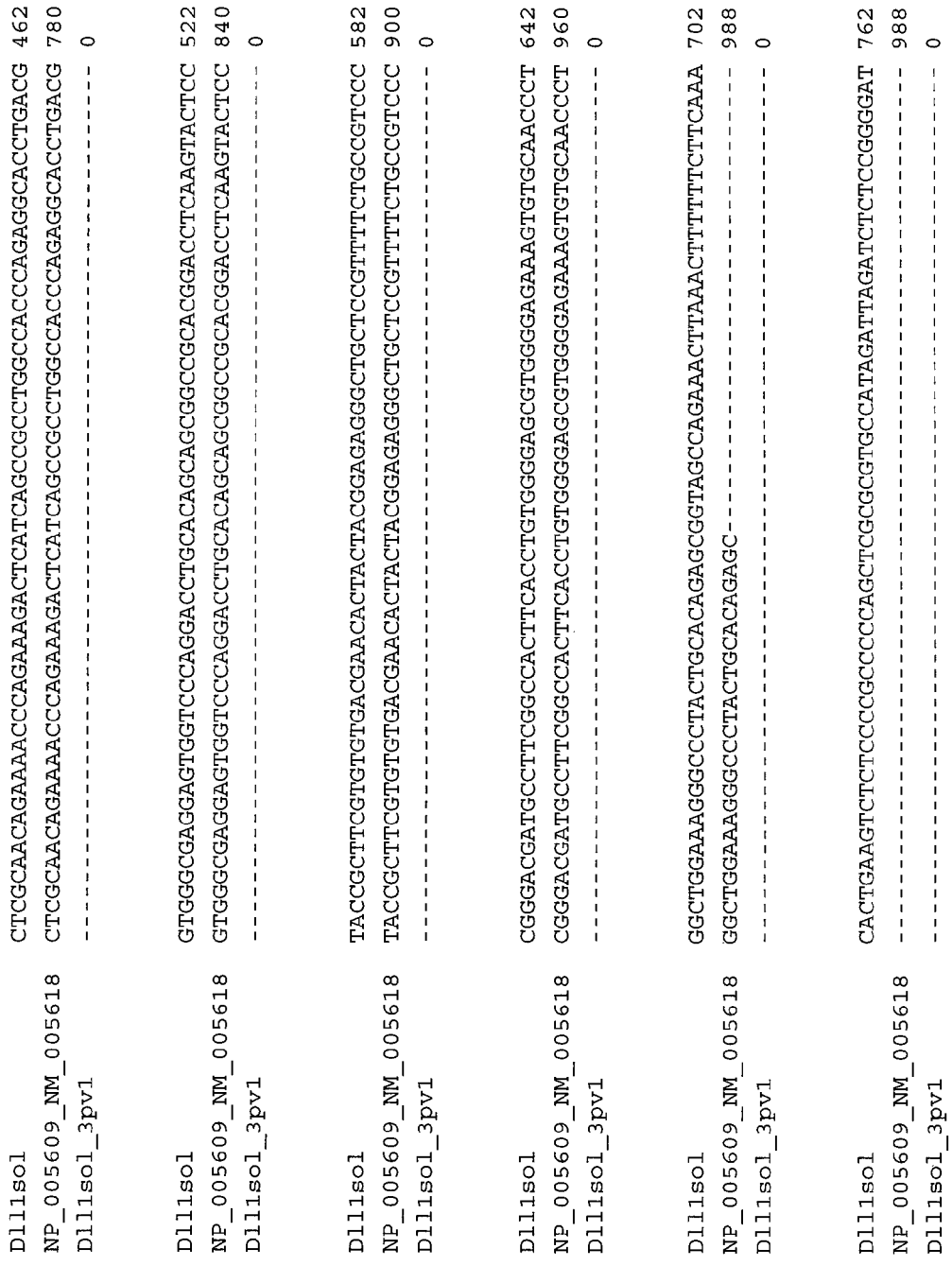
Figure 4F:

FIG. 4: Nucleotide sequence alignment of DLL1sol (SEQ ID NO:8) compared to the DLL1 sequence NP_005609_NM_005618 (SEQ ID NO: 10) and Dll1sol_3v1 (SEQ ID NO:11). "N" indicates unavailable nucleotide sequence. The periods (.) indicate semi-conservative amino acid changes. The alignment was generated using Clustal Format for T-COFFEE Version_1.37, CPU=0.00 sec, score=99, Nseq=3, and Len=3305.

DETAILED DESCRIPTION OF THE INVENTION

Definitions

The terms "polynucleotide," "nucleic acid," and "nucleic acid molecule" are used interchangeably to refer to polymeric forms of nucleotides of any length. The polynucleotides can contain deoxyribonucleotides, ribonucleotides, and/or their analogs. Nucleotides can have any three-dimensional structure, and can perform any function, known or as yet unknown. The term "polynucleotide" includes single-stranded, double-stranded and triple helical molecules that may encode a full-length gene or a biologically active fragment thereof.

The following are non-limiting embodiments of polynucleotides: a gene or gene fragment, exons, introns, mRNA, tRNA, rRNA, antisense molecules, RNAi, ribozymes, cDNA, recombinant polynucleotides, branched polynucleotides, plasmids, vectors, isolated DNA of any sequence, isolated RNA of any sequence, nucleic acid probes, and primers. Polynucleotides include splice variants of an mRNA. Nucleic acids can be naturally occurring, e.g., DNA or RNA, or can be synthetic analogs, as known in the art. Such analogs are suitable as probes because they demonstrate superior stability under assay conditions. A nucleic acid molecule can also comprise modified nucleic acid molecules, such as methylated nucleic acid molecules, peptide nucleic acids, and nucleic acid molecule analogs. Analogs of purines and pyrimidines are known in the art.

"Oligonucleotide" may generally refer to polynucleotides of between about 5 and about 100 nucleotides of single- or double-stranded DNA. For the purposes of this disclosure, there is no upper limit to the length of an oligonucleotide. Oligonucleotides are also known as oligomers or oligos and can be isolated from genes, or chemically synthesized by methods known in the art.

A "complement" of a nucleic acid molecule is a one that is comprised of its complementary base pairs. Deoxyribonucleotides with the base adenine are complementary to those with the base thymidine, and deoxyribonucleotides with the base thymidine are complementary to those with the base adenine. Deoxyribonucleotides with the base cytosine are complementary to those with the base guanine, and deoxyribonucleotides with the base guanine are complementary to those with the base cytosine. Ribonucleotides with the base adenine are complementary to those with the base uracil, and deoxyribonucleotides with the base uracil are complementary to those with the base adenine. Ribonucleotides with the base cytosine are complementary to those with the base guanine, and deoxyribonucleotides with the base guanine are complementary to those with the base cytosine.

An "expression system" is any composition that permits protein synthesis when an expression vector is provided to the system. Expression systems are well-known by those skilled in the art. They include cell-free expression systems, e.g., wheat germ extract systems, rabbit reticulocyte systems, and frog oocyte systems. They also include systems that utilize host cells, such as E. coli expression systems, yeast expression systems, insect expression systems, insect expression systems, and mammalian expression systems.

A "translation system" is a system that supports the process by which the sequence of nucleotides in a messenger RNA molecule directs the incorporation of amino acids into a protein or polypeptide. To "allow polypeptide synthesis" is to permit the incorporation of amino acids into a protein or polypeptide.

A "vector" is a polynucleotide construct. Vectors typically include at least one origin of replication, at least one site for insertion of heterologous nucleic acid (e.g., in the form of a polylinker with multiple, tightly clustered, single cutting restriction endonuclease recognition sites), and at least one selectable marker. A wide variety of vectors are known in the art. Vectors include, but are not limited to, plasmids; cosmids; viral vectors; human, yeast, bacterial, P1-derived artificial chromosomes (HAC's, YAC's, BAC's, PAC's, etc.), and mini-chromosomes (Ausubel, et al.; Jones et al., 1998a; Jones et al., 1998b). Vectors can provide for nucleic acid expression, for nucleic acid propagation, or both.

The term "host cell" includes an individual cell or cell culture which can be or has been a recipient of any recombinant vector(s) or isolated polynucleotide of the invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a polynucleotide of the invention.

"Transfecting a host cell" refers to introducing a foreign DNA molecule into a cell. It is usually followed by expression of one or more genes in the newly introduced DNA.

A "plurality of cells that produce the polypeptide" refers to at least two cells that produce a defined polypeptide.

A "cell-free composition" is the product of mixing or combining one or more elements, which includes no intact cells.

The term "biologically active fragment" of a nucleotide refers to a nucleotide sequence that encodes a biologically active polypeptide, which is defined below. A biologically active fragment of a polynucleotide also includes a polynucleotide that can be detected as unique for the polynucleotide molecule, or that can be used as a primer in PCR.

The term "degenerate sequence" or "degenerate variant" of a reference nucleic acid sequence refers to all nucleic acid sequences that can be directly translated, using the standard genetic code, to provide an amino acid sequence identical to that translated from the reference nucleic acid sequence.

A "promoter" is a nucleotide sequence present in DNA, to which RNA polymerase binds to begin transcription. Promoters vary in strength, promoter sequences at which RNA polymerase initiates transcription at a high frequency are classified as "strong", and those with a low frequency of initiation, as "weak." Promoters can be naturally occurring or engineered sequences. A "constitutive promoter" is one that is active unless repressed. An "inducible promoter" is one that functions as a promoter upon receiving a predetermined stimulus. A "conditionally active" promoter is one that s active only under defined circumstances, e.g., the cre-lox promoter. A "tissue-specific" promoter only permits transcription is selected tissues, e.g., the α-1 antitrypsin promoter is selective for lung tissue, albumin promoters are selective for hepatocytes, tyrosine hydrolase promoters are selective for melanocytes, villin promoters are selective for intestinal epithelium, glial fibrillary acidic protein promoters are selective for astrocytes, myelin basic protein promoters are selective for glial cells, and the immunoglobulin gene enhancer promoter is selective for B lymphocytes.

"Contiguous" refers to a state of being in actual contact, being adjacent to, touching along a boundary or at a point, next or near in time or sequence, or touching or connected throughout in an unbroken sequence.

The terms "polypeptide" and "protein," used interchangeably herein, refer to a polymeric form of amino acids of any length, which can include coded and non-coded amino acids, chemically or biochemically modified or derivatized amino acids, and polypeptides having modified peptide backbones.

By "polypeptide" is further meant an amino acid sequence encoded by an open reading frame, including the full length protein and fragments thereof. The term includes "biologically active fragments", which have structural, regulatory, or biochemical functions of the full-length protein. Biologically active fragments can correspond to functional domains, e.g., a signal peptide or leader sequence, an enzyme active site including an cleavage site and an enzyme catalytic site, a domain for interaction with other protein(s), a domain for binding DNA, a regulatory domain, a consensus domain that is shared with other members of the same protein family, such as a kinase family, an extracellular domain that may act as a target for antibody production, an extracellular domain that may be cleaved to become a soluble receptor or a ligand for a receptor, and an intracellular fragment of a transmembrane protein that participates in signal transduction. It includes fusions of the subject polypeptides to other proteins or parts thereof.

Biologically active peptide fragments of the invention exhibit activity similar, but not necessarily identical, to an activity of a polypeptide of the invention. The biological activity of the fragments can include an improved desired activity, or a decreased undesirable activity. For example, a biologically active fragment of a polypeptide includes one that can participate in a biological reaction, e.g., as a transcription factor that combines with other transcription factors for initiation of transcription; that can stimulate an immune response, such as production of antibodies; or that can participate in signal transduction by binding to receptors, or activating enzymes or substrates.

"Fusion proteins" are proteins or polypeptides that contain amino acids from more than one source. They encompass polypeptides with changed or inserted amino acids, and polypeptides fused to one or more detectable reporter proteins. They also include, but are not limited to, fusion proteins with a heterologous amino acid sequence, fusion proteins with heterologous and homologous leader sequences, fusion proteins with or without N-terminal methionine residues, and immunologically tagged proteins.

"Naked protein" refers to a protein or polypeptide consisting of an amino acid sequence. A "chemically modified" protein or polypeptide refers to a protein or polypeptide with one or more adaptations that are not produced by nature.

A "receptor" is a polypeptide that binds to a specific extracellular molecule and initiates a cellular response. A receptor can be part of a cell membrane, or it can be soluble; it can be on the cell surface or inside the cell. Soluble receptors include extracellular fragments of transmembrane cell surface receptors that have been proteolytically cleaved, as well as luminal fragments of receptors that have been proteolytically cleaved.

A "ligand" is any molecule that binds to a specific site on another molecule.

"Agonist" refers to a substance that mimics the function of an active molecule. Agonists include, but are not limited to, drugs, hormones, antibodies, and neurotransmitters, as well as analogues and fragments thereof.

"Antagonist" refers to a molecule that competes for the binding sites of an agonist, but does not induce an active response. Antagonists include, but are not limited to, drugs, hormones, antibodies, and neurotransmitters, as well as analogues and fragments thereof.

As used herein, the term "antibody" encompasses polyclonal and monoclonal antibody preparations, altered antibodies, and hybrid (chimeric) antibody molecules (see, for example, Winter and Milstein, 1991; and U.S. Pat. No. 4,816, 567; Morrison et al., 1984; Neuberger et al., 1984; Takeda et al., 1985); F(ab')$_2$ and F(ab) fragments; Fv molecules, i.e., noncovalent heterodimers, (see, for example, Inbar et al., 1972; and Ehrlich et al., 1980); single-chain Fv molecules (sFv) (see, for example, Huston et al., 1988); dimeric and trimeric antibody fragment constructs; minibodies (see, for example, Pack and Pluckthun, 1992); Cumber et al., 1992); humanized antibody molecules (see, for example, Riechmann et al., 1988); Verhoeyan et al., 1988); and any functional fragments obtained from such molecules, wherein such fragments retain specific binding properties, and preparations thereof. As used herein, the term "monoclonal antibody" refers to an antibody composition having a homogeneous antibody population. The term is not limited regarding the species or source of the antibody, nor is it intended to be limited by the manner in which it is made. The term encompasses whole immunoglobulins.

"*E. coli*," or "*Escherichia coli*," is a bacterial species in the family Enterobacteriaceae; it includes all members of the species, including, but not limited to *E. coli* 042, *E. coli* B, *E. coli* CFT073, *E. coli* E2348, *E. coli* K12, *E. coli* 011:H-, *E. coli* 0127:H6, *E. coli* O157:H7, *E. coli* O157:H7 EDL933, and *E. coli* 06.

As used herein, a "stem cell" is a pluripotent or multipotent cell with the ability to self-renew, to remain undifferentiated, and to become differentiated.

"Lineage-restricted progenitor cells" are cells with the capacity to differentiate into a particular lineage. They are biological ancestors of differentiated cells, and, while they may retain their present low level of undifferentiation, they can also differentiate into more specialized cells of a particular lineage. For example, lineage-restricted hematopoeitic progenitor cells can differentiate into blood cells, but not into muscle cells, because blood cells and muscle cells do not share the same biological lineage. A lineage-restricted progenitor cell can further differentiate into a cell capable of generating only restricted cell populations within that lineage, e.g., a hematopoeitic progenitor that is capable of generating cells that can form any type of blood cell can further differentiate into a cell that is capable only of forming red blood cells.

An "increase in multilineage cells" is an increase in the number of cells that have the capacity to commit to differentiating into one or more cell types. "Stimulating the production of hematopoeitic cells" refers to a process of causing a response that includes yielding cells that are capable of generating blood cells.

"Biological sample," as used herein, includes biological fluids such as blood, serum, plasma, urine, cerebrospinal fluid, tears, saliva, lymph, dialysis fluid, lavage fluid, semen, and other liquid samples or tissues of biological origin. It includes cells or cells derived therefrom and the progeny thereof, including cells in culture, cell supernatants, and cell lysates. It includes organ or tissue culture derived fluids, tissue biopsy samples, tumor biopsy samples, stool samples, and fluids extracted from physiological tissues. Cells dissociated from solid tissues, tissue sections, and cell lysates are included. The definition also includes samples that have been manipulated in any way after their procurement, such as by treatment with reagents, solubilization, or enrichment for certain components, such as polynucleotides or polypeptides. Also included in the term are derivatives and fractions of biological samples. A biological sample can be used in a diagnostic or monitoring assay.

To "determine the presence of" a substance is to detect that substance in isolation or as part of a composition. Detection methods of the invention can be qualitative or quantitative. Thus, as used herein, the terms "detection," "identification," and "determination," refer to both qualitative and quantitative determinations, and include "measuring."

The term "modulate" encompasses an increase or a decrease, a stimulation, inhibition or blockage in the measured activity when compared to a suitable control. "Modulation" of expression levels includes increasing the level and decreasing the level of a mRNA or polypeptide of interest encoded by a polynucleotide of the invention when compared to a control lacking the agent being tested. "Modulation" of cellular function includes increasing the level and decreasing the level of any physiologic or pathologic action of a cell. In some embodiments, agents of particular interest are those which inhibit a biological activity of a subject polypeptide, and/or which reduce a level of a subject polypeptide in a cell, and/or which reduce a level of a subject mRNA in a cell and/or which reduce the release of a subject polypeptide from a eukaryotic cell. In other embodiments, agents of interest are those that increase polypeptide activity.

To "regulate" is to govern or direct; it also refers to the process of providing order, method, or uniformity. "Regulation" is encompassed within modulation, and further encompasses the process of fixing or adjusting a time, amount, degree, or rate.

To "interact" is defined as the process of acting upon one another, and includes to coact, interplay, or interreact. "Determining whether interaction has occurred" means to employ any means that provides an indication that one or more molecules have interacted. Methods of determining whether nucleic acids have interacted include hybridization methods that are well-known in the art. Methods of determining whether proteins or polypeptides have interacted include the use of detectable markers, detection of a binding complex between a polypeptide and an interacting polypeptide or other macromolecule, e.g., DNA, RNA, lipids, or polysaccharides. Examples of suitable methods include a yeast two-hybrid method, a mammalian cell two-hybrid method, a FRET assay, a BRET assay, a fluorescence quenching assay, a fluorescence anisotropy assay, and an immunological assay.

A "target cell" is a cell that is designated to be influenced or changed by an action or event.

To "differentiate" is to develop differential characteristics. It encompasses a cell changing to an overtly specialized cell type.

The terms "patient," "subject," and "individual," used interchangeably herein, refer to a mammal, including, but not limited to, humans, murines, simians, felines, canines, equines, bovines, porcines, ovines, caprines, mammalian farm animals, mammalian sport animals, and mammalian pets.

"Treatment," as used herein, covers any treatment of a condition or disease in an animal, including a human, and includes inhibiting the condition or disease, i.e., arresting its development, or relieving the condition or disease, i.e., causing regression of the condition or disease, or restoring or repairing a lost, missing or defective function, or stimulating an inefficient process. "Prophylaxis," as used herein includes preventing a condition or disease from occurring or recurring in a subject who may be predisposed to the condition or disease but has not yet been diagnosed as having it. Treatment and prophylaxis can be administered to an organism, or to a cell in vivo, in vitro, or ex vivo, and the cell subsequently administered to the subject.

A "pharmaceutically acceptable carrier" refers to a non-toxic solid, semisolid or liquid filler, diluent, encapsulating material, or formulation auxiliary of any conventional type. A pharmaceutically acceptable carrier is non-toxic to recipients at the dosages and concentrations employed and is compatible with other ingredients of the formulation. For example, the carrier for a formulation containing polypeptides does not include oxidizing agents and other compounds that are known to be deleterious to polypeptides. Suitable carriers include, but are not limited to, water, dextrose, glycerol, saline, ethanol, and combinations thereof. The carrier can contain additional agents such as wetting or emulsifying agents, pH buffering agents, or adjuvants which enhance the effectiveness of the formulation. Topical carriers include liquid petroleum, isopropyl palmitate, polyethylene glycol, ethanol (95%), polyoxyethylene monolaurate (5%) in water, or sodium lauryl sulfate (5%) in water. Other materials such as anti-oxidants, humectants, viscosity stabilizers, and similar agents can be added as necessary. Percutaneous penetration enhancers such as Azone can also be included.

Before the present invention is further described, it is to be understood that this invention is not limited to particular embodiments described. It is also to be understood that the terminology used herein is for the purpose of describing particular embodiments only, and is not intended to be limiting, since the scope of the present invention will be limited only by the appended claims.

Protein Expression Systems

Expression Vectors

A recombinant vector or construct that includes a nucleic acid of the invention is useful for propagating a nucleic acid in a host cell. Vectors can transfer nucleic acid between host cells derived from disparate organisms; these are known in the art as "shuttle vectors." Vectors can also insert a subject nucleic acid into a host cell's chromosome; these are known in the art as "insertion vectors." Vectors can express either sense or antisense RNA transcripts of the invention in vitro (e.g., in a cell-free system or within an in vitro cultured host cell); these are known in the art as "expression vectors." Expression vectors can also produce a subject polypeptide encoded by a subject nucleic acid.

The expression vectors of the invention provide a transcriptional and translational initiation region, which may be inducible or constitutive, where the coding region is operably linked under the transcriptional control of the transcriptional initiation region, and a transcriptional and translational termination region. These control regions can be native to a gene encoding the subject peptides, or can be derived from exogenous sources.

Prior to vector insertion, the DNA of interest will be obtained substantially free of other nucleic acid sequences, and will be at least about 50%, at least about 70%, at least about 80%, or at least about 90% free of the materials with which it is associated in nature. The DNA can be "recombinant," and flanked by one or more nucleotides with which it is not normally associated on a naturally occurring chromosome.

Expression vectors generally have convenient restriction sites located near the promoter sequence to provide for the insertion of nucleic acid sequences encoding heterologous proteins. A selectable marker operative in the expression host can be present. Expression cassettes can be prepared comprising a transcription initiation region, the gene or fragment thereof, and a transcriptional termination region.

Expressed proteins and polypeptides can be obtained from naturally occurring sources or produced synthetically. For example, the proteins can be derived from biological sources that express the proteins. The proteins can also be, derived synthetically, e.g., by expressing a recombinant gene encoding a protein of interest in a suitable host. Convenient protein purification procedures can be employed (Deutscher et al., 1990). For example, a lysate can be prepared from the original source, (e.g., a cell expressing endogenous polypeptide, or a cell comprising the expression vector expressing the polypeptide(s)), and purified using HPLC, exclusion chromatography, gel electrophoresis, or affinity chromatography.

The invention includes DNA sequences that allow for the expression of biologically active fragments of the polypeptides of the invention. These include functional epitopes or domains, at least about 8 amino acids in length, at least about 15 amino acids in length, or at least about 25 amino acids in length, or any of the above-described fragments, up to and including the complete open reading frame of the gene. After introduction of these DNA sequences, the cells containing the construct can be selected by means of a selectable marker, and the selected cells expanded and used as expression-competent host cells.

Cell-Free Expression Systems

Cell-free translation systems can be employed to produce proteins of the invention using RNAs derived from the DNA constructs of the present invention. Appropriate cloning and expression vectors containing SP6 or T7 promoter for use with prokaryotic and eukaryotic hosts are known (Sambrook, et al., 1989). These DNA constructs can be used to produce proteins in a rabbit reticulocyte lysate system, with wheat germ extracts, or with a frog oocyte system.

Expression in Host Cells

The invention further provides host cells, e.g., recombinant host cells, that comprise a subject nucleic acid, and host cells that comprise a recombinant vector. Subject host cells can be cultured in vitro, or can be part of a multicellular organism.

Host cells can comprise prokaryotes or eukaryotes that express proteins and polypeptides in accordance with conventional methods, the method depending on the purpose for expression. The invention includes, but is not limited to expression in bacteria, yeast, plants, insects, and mammals. For large scale production of the protein, a unicellular organism, such as *E. coli, B. subtilis, S. cerevisiae*, insect cells in combination with baculovirus vectors, or cells of a higher organism such as vertebrates, particularly mammals, e.g., COS 7 cells, can be used as the expression host cells. In some situations, it is desirable to express eukaryotic genes in eukaryotic cells, where the encoded protein will benefit from native folding and post-translational modifications.

When any of the above-referenced host cells, or other appropriate host cells or organisms, are used to duplicate and/or express the polynucleotides of the invention, the resulting duplicated nucleic acid, RNA, expressed protein, or polypeptide, is within the scope of the invention as a product of the host cell or organism. The product can be recovered by any appropriate means known in the art.

The sequence of a gene, including flanking promoter regions and coding regions, can be mutated in various ways known in the art to generate targeted changes in promoter strength or in the sequence of the encoded protein. The DNA sequence or protein product of such a mutation will usually be substantially similar to the sequences provided herein, for example, will differ by at least one nucleotide or amino acid, respectively, and may differ by at least two nucleotides or amino acids. The sequence changes may be substitutions, insertions, deletions, or a combination thereof. Deletions may further include larger changes, such as deletions of a domain or exon. Other modifications of interest include epitope tagging, e.g., with the FLAG system, or hemagluttinin. For studies of subcellular localization, fusion proteins with green fluorescent proteins (GFP) or other fluorescent proteins (e.g., those derived from Anthozoa species, derivatives of such proteins) may be used.

Techniques for in vitro mutagenesis of cloned genes are known. Examples of protocols for site specific mutagenesis may be found in Gustin and Burk, 1993; Barany, 1985; Colicelli et al., 1985; and Prentki and Krisch, 1984. Methods for site specific mutagenesis can be found in Sambrook et al., 1989; Weiner et al., 1993; Sayers et al., 1992; Jones and Winistorfer, 1992; Barton et al., 1990; Marotti and Tomich, 1989; and Zhu, 1989. Such mutated genes may be used to study structure-function relationships of the subject proteins, or to alter properties of the protein that affect its function or regulation.

One may also provide for expression of the gene, e.g., a subject gene, or variants thereof in cells or tissues where it is not normally expressed, at levels not normally present in such cells or tissues, or at abnormal times of development. One may also generate host cells (including host cells in transgenic animals) that comprise a heterologous nucleic acid molecule which encodes a polypeptide which functions to modulate expression of an endogenous promoter or other transcriptional regulatory region.

DNA constructs for homologous recombination will comprise at least a portion of the human gene or of a gene native to the species of the host animal, wherein the gene has the desired genetic modification(s), and includes regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al., 1990.

Specific cellular expression systems of interest include plants, bacteria, yeast, insect cells and mammalian cell-derived expression systems. Representative systems from each of these categories are provided below.

Plants

Expression systems in plants include those described in U.S. Pat. No. 6,096,546 and U.S. Pat. No. 6,127,145.

Bacteria

Expression systems in bacteria include those described by Chang et al., 1978; Goeddel et al., 1979; Goeddel et al., 1980; EP 0 036,776; U.S. Pat. No. 4,551,433; DeBoer et al., 1983; and Siebenlist et al., 1980.

Yeast

Expression systems in yeast include those described by Hinnen et al., 1978; Ito et al., 1983; Kurtz et al., 1986; Kunze et al., 1985; Gleeson et al., 1986; Roggenkamp et al., 1986; Das et al., 1984; De Louvencourt et al., 1983; Van den Berg et al., 1990; Kunze et al., 1985; Cregg et al., 1985; U.S. Pat. Nos. 4,837,148 and 4,929,555; Beach and Nurse, 1981; Davidow et al., 1985; Gaillardin et al., 1985; Ballance et al., 1983; Tilburn et al., 1983; Yelton et al., 1984; Kelly and Hynes, 1985; EP 0 244,234; WO 91/00357; and U.S. Pat. No. 6,080,559.

Insects

Expression systems for heterologous genes in insects includes those described in U.S. Pat. No. 4,745,051; Friesen et al., 1986; EP 0 127,839; EP 0 155,476; Vlak et al., 1988; Miller et al., 1988; Carbonell et al., 1988; Maeda et al., 1985; Lebacq-Verbeyden et al., 1988; Smith et al., 1985); Miyajima et al., 1987; and Martin et al., 1988. Numerous baculoviral strains and variants and corresponding permissive insect host cells are described in Luckow et al., 1988, Miller et al., 1986, and Maeda et al., 1985.

Mammals

Mammalian expression systems include those described in Dijkema et al., 1985; Gorman et al., 1982; Boshart et al., 1985; and U.S. Pat. No. 4,399,216. Additional features of mammalian expression are facilitated as described in Ham and Wallace, 1979; Barnes and Sato, 1980 U.S. Pat. Nos. 4,767,704, 4,657,866, 4,927,762, 4,560,655, WO 90/103430, WO 87/00195, and U.S. RE 30,985.

Reporter Systems

The invention provides reporter systems for activated signal transduction pathways; these systems include pathway-specific promoters linked to "readouts" which can be produced efficiently by introducing the reporter systems into non-human animals. The reporter systems are introduced into embryonic stem (ES) cells, which can be incorporated into one or more blastocysts, which can in turn be implanted into pseudo-pregnant non-human animals to produce chimeric animals expressing the reporter in a broad range of tissues.

Through this approach, transfecting a single ES cell can produce multiple transfected cell types, some of which may be otherwise difficult to transfect in their differentiated state. Substantially all the tissues of the resulting chimera have the potential to activate the reporter system upon responding to specific exogenous signals. The reporter systems can be specific for a single signal transduction pathway or can be expressed upon activation of any of a number of pathways. The reporter systems can also be specific for multiple integrated signaling pathways by including the relevant combination of pathway components, e.g., transcription factor binding sites. The different cell types of the chimeric animals can be used to detect pathway activation, for example, by growth or differentiation factors that bind to cell surface receptors and activate a pathway or pathways detected by the reporter. The cells can also be used in vivo and in vitro to measure the effect of signal transduction modulators, such as small molecules, or antibody agonists or antagonists of the pathway detected by the reporter system.

Transfected ES cells can be used to make chimeric animals that express the reporter in various specified tissues, such as by use of tissue-specific promoters. These chimeric animals can be used to test or determine which tissues respond to protein factors or small molecules administered to the animals. This in vivo reporter system can be used to test drug efficacy, toxicity, pharmacokinetics, and metabolism.

The invention provides a system for conducting in vivo and in vitro testing of signal transduction protein function, for expression or manufacture of proteins. The system provides targeting a gene to a locus, e.g., the ROSA 26 locus in mouse ES cells and allowing the transfected DNA to proliferate and differentiate in vitro. The ROSA 26 locus directs the ubiquitous expression of the heterologous gene (U.S. Pat. No. 6,461,864). For example, the effect of the transfected DNA on healthy or diseased cells can be monitored in vitro. Differentiation of cells, e.g., cardiomyocytes, hepatocytes, skeletal myocytes, etc. can be monitored by morphologic, histologic, and/or physiologic criteria.

The tissues of the chimeric mice or their progeny can be isolated and studied, or cells and/or cell lines can be isolated from the tissues and studied. Tissues and cells from any organ in the body, including heart, liver, lung, kidney, spleen, thymus, muscle, skin, blood, bone marrow, prostate, breast, stomach, brain, spinal cord, pancreas, ovary, testis, eye, and lymph node are suitable for use.

This in vivo reporter system can be used to test drug efficacy, toxicity, pharmacokinetics, and metabolism. Examining reporter gene expression in cells, tissues, and animals that have been treated with a candidate therapeutic agent provides information about the effect of the candidate agent on the signal transduction system or systems.

Fusion Proteins

The protein expression systems described above can produce fusion proteins that incorporate the polypeptides of the invention. Fusion proteins may comprise a subject polypeptide, or a fragment thereof, and another polypeptide other than a subject polypeptide ("the fusion partner") fused in-frame at the N-terminus and/or C-terminus of the subject polypeptide, or internally to the subject polypeptide. Suitable fusion partners include, but are not limited to, albumin and fetuin (Yao et al., 2004; pending U.S. provisional application filed Jul. 22, 2004, entitled Fusion Polypeptides of Human Fetuin and Therapeutically Active Polypeptides).

The polypeptides of the invention can be optimized for expression in each of the expression systems described above. For example, particular sequences can be introduced into the expression vector which optimize the expression of the protein in a yeast vector; other sequences can optimize the expression of the protein in a plant vector, and so forth. These sequences are known to skilled artisans and are described in the cited references.

In addition to the polypeptides of the invention, these fusion proteins additionally contain one or more polypeptide components that may provide a functional advantage. Fusion proteins can stabilize the structure and modify the biological activity of the expressed protein. For example, they can be used to increase protein secretion, ease of purification, production, stability, or to provide a detectable marker.

Polypeptides can be encoded that are secreted from the cell by the incorporation of leader sequences that direct the protein to the membrane for secretion. These leader sequences are specific to the host cell, are known to skilled artisans, and are also cited in the references. The invention includes appropriate restriction enzyme sites for cloning into the vector.

In addition to facilitating the secretion of these fusion proteins, the invention provides for facilitating their production. This can be accomplished in a number of ways, including producing multiple copies, employing strong promoters, and increasing their intracellular stability, e.g., by fusion with beta-galactosidase.

The invention also provides for facilitating the purification of these fusion proteins. Fusion with a selectable marker can facilitate purification by affinity chromatography. For example, fusion with the selectable marker glutathione S-transferase (GST) produces polypeptides that can be detected with antibodies directed against GST, isolated by affinity chromatography on glutathione-sepharose; the GST marker can then be removed by thrombin cleavage. Polypeptides that provide for binding to metal ions are also suitable for affinity purification. For example, a fusion protein that incorporates $His_n$, where n=3-10, e.g., 6×His-tag (SEQ ID NO:14) can be used to isolate a protein by affinity chromatography using nickel.

Suitable fusion partners that can be used to detect the fusion protein include all polypeptides that can bind to an antibody specific to the fusion partner (e.g., epitope tags, such as hemagglutinin, FLAG, and c-myc); polypeptides that provide a detectable signal (e.g., a fluorescent protein, e.g., a green fluorescent protein, a fluorescent protein from an Anthozoan species; β-galactosidase; and luciferase). For example, where the fusion partner provides an immunologically recognizable epitope, an epitope-specific antibody can be used to quantitatively detect the level of polypeptide. In some embodiments, the fusion partner provides a detectable signal, and in these embodiments, the detection method is chosen based on the type of signal generated by the fusion partner. For example, where the fusion partner is a fluorescent protein, fluorescence is measured.

Where the fusion partner is an enzyme that yields a detectable product, the product can be detected using an appropriate means. For example, β-galactosidase can, depending on the substrate, yield a colored product that can detected with a spectrophotometer, and the fluorescent protein luciferase can yield a luminescent product detectable with a luminometer.

Fluorescent proteins include, but are not limited to, a green fluorescent protein (GFP), including, but not limited to, a "humanized" version of a GFP, e.g., wherein codons of the naturally-occurring nucleotide sequence are changed to more closely match human codon bias; a GFP derived from *Aequoria victoria* or a derivative thereof, e.g., a "humanized" derivative such as Enhanced GFP, which are available commercially, e.g., from Clontech, Inc.; a GFP from another species such as *Renilla reniformis, Renilla mulleri*, or *Ptilosarcus guernyi*, as described in, e.g., WO 99/49019 and Peelle et al., 2001; "humanized" recombinant GFP (hrGFP) (Stratagene); any of a variety of fluorescent and colored proteins from Anthozoan species, as described in, e.g., Matz et al., 1999.

Modulation of Gene Expression and Polypeptide Function
Inhibition by Antisense RNA, siRNA, and Peptide Aptamers In some embodiments of the invention, an active agent modulates the expression of a gene. For example, antisense molecules can be used to down-regulate expression of the subject genes in cells. The antisense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g., by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, usually not more than about 35 nucleotides in length, and usually not more than about 50, and not more than about 500, where the length is governed by efficiency of inhibition, specificity, including absence of cross-reactivity, and the like. Short oligonucleotides, of from 7 to 8 bases in length, can be strong and selective inhibitors of gene expression (Wagner et al., 1996).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Suitable sequences may be chosen from the extracellular region of the protein, which is predicted to influence hematopoietic function, based on the homology of the human protein with murine kirre. Suitable sequences may be chosen from the immunoglobulin-like extracellular domains, the signal sequence, the PDZ-binding motif, the metalloproteinase cleavage site, the kinase or phosphatase consensus sequences, or any other motif that is known or predicted to play a role in the function of the protein.

Antisense oligonucleotides can be chemically synthesized by methods known in the art (Wagner et al., 1993; Milligan et al., 1993). Preferred oligonucleotides are chemically modified from the native phosphodiester structure, in order to increase their intracellular stability and binding affinity. A number of such modifications have been described in the literature, which modifications alter the chemistry of the backbone, sugars or heterocyclic bases.

As an alternative to antisense inhibitors, catalytic nucleic acid compounds, e.g., ribozymes, anti-sense conjugates, interfering RNA, etc. can be used to inhibit gene expression. Ribozymes can be synthesized in vitro and administered to the patient, or encoded in an expression vector, from which the ribozyme is synthesized in the targeted cell (WO 95/23225; Beigelman et al., 1995). Examples of oligonucleotides with catalytic activity are described in WO 95/06764. Conjugates of anti-sense ODN with a metal complex, e.g., terpyridylCu(II), capable of mediating mRNA hydrolysis are described in Bashkin et al., 1995).

Small interfering RNA (siRNA) can also be used as an inhibitor. Small interfering RNA can be used to screen for biologically active agents by administering siRNA compositions to cells, monitoring for a change in a readable biological activity, and repeating the administration and monitoring with a subset of the plurality of siRNA compositions to determine which silenced gene is responsible for the change, then identifying the transcriptional or translational gene product of the silenced gene. The transcriptional or translational product so identified may represent a biologically active agent, responsible for the change which is determined by the readable biological activity.

Small interfering RNA compositions, including the libraries of the invention, can be used to screen populations of transfected cells for phenotypic changes. Cells with the desired phenotype can be recovered, and the siRNA construct can be characterized. The screening can be performed using oligonucleotides specific to any open reading frame, including enzymatically fragmented, open reading frames, e.g., with restriction endonucleases. The screening can also be performed using random siRNA libraries, including enzymatically fragmented libraries, e.g., with restriction endonucleases.

The invention provides a method of using siRNA to identify one or more specific siRNA molecules effective against one or more delta ligands or Notch receptors. This method can be performed by administering the composition to cells expressing the mRNA, monitoring for a change in a readable biological activity, e.g., activity relevant to a disease condition, and repeating the administration and monitoring with a subset of a plurality of siRNA molecules, thereby identifying one or more specific siRNA molecules effective against one or more genes relevant to a disease condition. This method includes using one or more siRNA molecules for treating or preventing a disease, by administering the identified siRNA to patient in an amount effective to inhibit one or more genes relevant to the disease. This method can be performed, e.g., by gene therapy, described in more detail below, by administering an effective amount of the identified specific siRNA to a patient. This method can also be performed by administering an effective amount of the identified specific siRNA to a patient by administering a nucleic acid vaccine, either with or without an adjuvant, also described in more detail below. The siRNA molecules and compositions of the invention can be also used in diagnosing a given disease or abnormal condition by administering any of the siRNA molecules or compositions of the invention to a biological sample and monitoring for a change in a readable biological activity to identify the disease or abnormal condition.

Another suitable agent for reducing an activity of a subject polypeptide is a peptide aptamer. Peptide aptamers are peptides or small polypeptides that act as dominant inhibitors of protein function; they specifically bind to target proteins, blocking their function (Kolonin and Finley, 1998). Due to the highly selective nature of peptide aptamers, they may be used not only to target a specific protein, but also to target specific functions of a given protein (e.g., a signaling function). Further, peptide aptamers may be expressed in a controlled fashion by use of promoters which regulate expression in a temporal, spatial or inducible manner. Peptide aptamers act dominantly; therefore, they can be used to analyze proteins for which loss-of-function mutants are not available.

Stabilization with Hydrophilic Polymers

The peptides of the invention can be modified with or covalently coupled to one or more of a variety of hydrophilic polymers to increase their solubility and circulation half-life. Suitable nonproteinaceous hydrophilic polymers for coupling to a peptide include, but are not limited to, polyalkylethers as exemplified by polyethylene glycol and polypropylene glycol, polylactic acid, polyglycolic acid, polyoxyalkenes, polyvinylalcohol, polyvinylpyrrolidone, cellulose and cellulose derivatives, dextran and dextran derivatives, etc. Generally, such hydrophilic polymers have an average molecular weight ranging from about 500 to about 100,000 daltons, from about 2,000 to about 40,000 daltons, or from about 5,000 to about 20,000 daltons. The peptide can be derivatized with or coupled to such polymers using any of the methods set forth in Zallipsky 1995; Monfardini et al., 1995; U.S. Pat. Nos. 4,791,192; 4,670,417; 4,640,835; 4,496,689; 4,301,144; 4,179,337 and WO 95/34326.

Conjugating biomolecules with polyethylene glycol (PEG), a process known as pegylation, increases the circulating half-life of therapeutic proteins (Molineux, 2002). Polyethylene glycols are nontoxic water-soluble polymers that, owing to their large hydrodynamic volume, create a shield around the pegylated drug, thus protecting it from renal clearance, enzymatic degradation, and recognition by cells of the immune system.

Pegylated agents have improved pharmacokinetics that permit dosing schedules that are more convenient and more acceptable to patients. This improved pharmacokinetic profile may decrease adverse effects caused by the large variations in peak-to-trough plasma drug concentrations associated with frequent administration and by the immunogenicity of unmodified proteins (Harris et al., 2001). In addition, pegylated proteins may have reduced immunogenicity because PEG-induced steric hindrance can prevent immune recognition (Harris et al., 2001).

Regulating the Growth or Division of a Target Cell

The invention provides polypeptides that can function as agonists, e.g., by functioning as a ligand. These polypeptides can also function as antagonists upon their release, e.g., by functioning as a soluble receptor. These cleaved agonists and antagonists can exert a physiologic or pathologic influence, for example by influencing the cell to differentiate or to remain in an undifferentiated state.

The transmembrane proteins of the invention sense the extracellular environment, and, in response, initiate signaling pathways that regulate cell migration, growth, and survival. These proteins can function as antigens, and as receptors, both when they are present in the membrane, and when they have been cleaved to a soluble form. These transmembrane proteins can be involved in all aspects of sensing the extracellular environment, and ensuing signal transduction events.

Transmembrane receptors are also involved in pathogenesis. For example, they mediate viral entry into cells, promulgate the inflammatory response, and are involved in the regulation of abnormal cell proliferation. The transmembrane proteins of the invention can, under genetically or environmentally-induced conditions, mediate abnormal differentiation. Failure to induce physiologically appropriate differentiation can result in an overproduction or proliferation of inappropriately immature cells, e.g., blast cells, that are unable to perform the functions of differentiated cells, and which may be inappropriately stimulated to proliferate as a result of the absence of a functional differentiated cell.

The extracellular domains of polypeptides of the invention can have bioactive properties that can be exerted on target cells. The bioactive properties of the extracellular domains of the polypeptides of the invention include the growth and differentiation of target cells. These extracellular domains can exert their bioactive properties on target cells in vivo, either by being cleaved from the cell, e.g., by proteolytic cleavage, and migrating to the vicinity of a target cell, or by virtue of the extracellular domain of the polypeptide of the invention having proximity to the target cell. These extracellular domains can also exert their bioactive properties on target cells in vitro.

Target cells can be maintained in the laboratory using methods known to skilled artisans. Potential targets for the bioactive extracellular domains of the polypeptides of the invention include stem cells. Potential targets also include cells that are intermediates in the differentiation pathways that lead from stem cells to fully differentiated cells. The bioactive extracellular domains of the polypeptides of the invention can modulate the growth or differentiation of target cells. They can increase or decrease the growth of target cells. They can keep target stem cells in an undifferentiated state, or they can induce them to differentiate.

Detection of Membrane Proteins Supportive of Stem Cells

Methods of Detecting the Polypeptides

The present invention further provides methods for detecting and measuring proteins, including human membrane proteins that support stem cells, their biologically active fragments, and related fusion proteins. The methods involve detecting the polypeptides in a biological sample, using a specific antibody. The methods will be performed by contacting the sample with an antibody specific for a subject polypeptide; and detecting binding between the antibody and molecules of the sample.

Detection of specific binding of the antibody, when compared to a suitable control, is an indication that a subject polypeptide is present in the sample. Suitable controls include a sample known not to contain a subject polypeptide; and a sample contacted with an antibody not specific for the subject polypeptide, e.g., an anti-idiotype antibody. A variety of methods to detect specific antibody-antigen interactions are known in the art and can be used in the method, including, but not limited to, standard immunohistological methods, immunoprecipitation, an enzyme immunoassay, and a radioimmunoassay. These methods are known to those skilled in the art (Harlow et al., 1998; Harlow and Lane, 1988).

The specific antibody will be detectably labeled, either directly or indirectly. Direct labels include radioisotopes; enzymes with detectable substrates (e.g., luciferase, β-galactosidase, and peroxidase); fluorescent labels (e.g., fluorescein and its derivatives, rhodamine dyes, and cyanine dyes); fluorescence emitting metals, (e.g., $^{152}$Eu, or others of the lanthanide series, attached to the antibody through metal chelating groups such as EDTA); chemiluminescent compounds (e.g., luminol, isoluminol, and acridinium salts) and bioluminescent compounds (e.g., luciferin, aequorin, and green fluorescent protein). Indirect labels include second antibodies specific for the specific antibodies. The second antibody can be labeled as described above. Either the first or second antibody can also be labeled with a member of a specific binding pair, e.g., biotin or peroxidase. An indirect method can then be employed to detect either the first or second antibody by contacting the antibody with a second member of the specific binding pair, e.g. avidin/streptavidin, or antiperoxidase. The second member of the pair can further be attached to a detectable molecule, i.e. an antibody molecule.

The antibody may be attached, or coupled, to an insoluble support, such as a polystyrene plate, or a bead, or a sheet of supporting material, such as nitrocellulose. The biological sample can be brought into contact with the support, which is capable of immobilizing biological samples containing cells, cell particles, or soluble polypeptides. The support may then be washed with suitable buffers, followed by contact with a detectably-labeled specific antibody.

The invention provides antibodies that can distinguish the variant DLL1 sequences of the invention from currently known DLL1 sequences. These antibodies can distinguish polypeptides that differ by no more than one amino acid (U.S. Pat. No. 6,656,467). They have high affinity constants, i.e., in the range of approximately $10^{-10}$M, and are produced, for example, by genetically engineering appropriate antibody gene sequences, according to the method described by Young et al., in U.S. Pat. No. 6,656,467.

A number of methods are available for determining the expression level of a gene or protein in a particular sample. Pre-treatment diagnosis may be performed by a number of methods to determine the absence or presence or altered amounts of normal or abnormal polypeptide in a patient sample. For example, detection may utilize staining of bone marrow cells or histological sections with labeled antibodies, performed in accordance with conventional methods (Harlow et al., 1998; Harlow and Lane, 1988).

Diagnostic methods in which the level of expression is of interest will typically involve comparing the nucleic acid abundance of a sample of interest with that of a control value to determine any relative differences. These differences can then be measured qualitatively and/or quantitatively, and differences related to the presence or absence of an abnormal expression pattern. A variety of different methods for determining the nucleic acid abundance in a sample are known to those of skill in the art; particular methods of interest include those described in: Soares, 1997; Pietu et al., 1996; Stolz and Tuan, 1996; Zhao et al., 1995; Chalifour et al., 1994; Raval, 1994; McGraw, 1984; and Hong, 1982. Also of interest are the methods disclosed in WO 97/27317.

Methods of Detecting the Polynucleotide mRNAs

The present invention further provides methods for detecting and measuring RNAs that encode Notch receptor ligands, their biologically active fragments, and related fusion proteins. These methods can be used, for example, to assess whether a test compound affects gene expression of these polypeptides, either directly or indirectly. The methods generally comprise contacting a biological sample with a polynucleotide of the invention under conditions which allow hybridization; and detecting any hybridization that occurs.

Detection of hybridization, when compared to a suitable control, is an indication of the presence in the sample of a subject polynucleotide. Appropriate controls include, for example, a sample which is known not to contain subject polynucleotide mRNA, and use of a labeled polynucleotide of the same "sense" as a subject polynucleotide mRNA. Conditions which allow hybridization are known in the art. Detection can be accomplished by any known method, including, but not limited to, in situ hybridization, PCR, RT-PCR, and "Northern" or RNA blotting, or combinations of such techniques, using a suitably labeled subject polynucleotide. Specific hybridization can be determined by comparison to appropriate controls.

A variety of labels and labeling methods for polynucleotides are known in the art and can be used in the assay methods of the invention. These include radioisotopes; enzymes with detectable substrates, fluorescent labels, fluorescence emitting metals, chemiluminescent compounds, and bioluminescent compounds.

Hybridization reactions can be performed under conditions of different stringency, and the stringency can be adjusted to match the desired level of sensitivity of the assay under specific conditions. Conditions that increase stringency of hybridization reactions are known in the art (Sambrook et al., 1989). Moreover, a person skilled in the art would know how to modify the conditions as necessary for the degree of stringency required for a particular assay.

In some embodiments, the detection methods involve generating a cDNA copy of an mRNA molecule in a biological sample, and amplifying the cDNA using a pair of isolated nucleic acid molecules that serve as forward and reverse primers in an amplification reaction (e.g., a polymerase chain reaction). Each of the nucleic acid molecules in the pair of nuclei acid molecules is from about 10 to 200 nucleotides in length, the first nucleic acid molecule of the pair comprising a sequence of at least 10 contiguous nucleotides having 100% sequence identity to a nucleic acid sequence shown in the Figures, and the second nucleic acid molecule of the pair comprising a sequence of at least 10 contiguous nucleotides having 100% sequence identity to the reverse complement of a nucleic acid sequence set forth in SEQ ID NO: 1, SEQ ID NO: 2, SEQ ID NO: 8, or SEQ ID NO: 9, wherein the sequence of the second nucleic acid molecule is located 3' of the nucleic acid sequence of the first nucleic acid molecule. The primer nucleic acids are prepared using any known method, e.g., automated synthesis, and the like. The primer pairs are chosen such that they specifically amplify a cDNA copy of an mRNA encoding a subject polypeptide.

Methods using PCR amplification can be performed on the DNA from a single cell, although it is convenient to use at least about $10^5$ cells. The use of the polymerase chain reaction is described in Saiki et al., 1988, and a review of current techniques may be found in Sambrook, et al., 1989; McPherson, et al., 2000; and Dieffenbach and Dveksler, 1995.

A number of methods are available for analyzing nucleic acids for the presence of a specific sequence, e.g. a disease associated polymorphism. Where large amounts of DNA are available, genomic DNA is used directly. Alternatively, the region of interest is cloned into a suitable vector and grown in sufficient quantity for analysis. Cells that express the gene may be used as a source of mRNA, which may be assayed directly or reverse transcribed into cDNA for analysis. The nucleic acid may be amplified by conventional techniques, such as the polymerase chain reaction (PCR), to provide sufficient amounts for analysis. Alternatively, various methods are known in the art that utilize oligonucleotide ligation as a means of detecting polymorphisms (Riley, et al., 1990; Delahunty, et al., 1996).

Biochemical studies can then be performed to determine whether a detected sequence polymorphism in a coding or control region is associated with disease. Disease-associated polymorphisms may include deletion or truncation of the gene, mutations that alter expression level, that affect the activity of the protein, etc. Changes in the promoter or enhancer sequence that may affect expression levels of the subject genes can be compared to expression levels of the normal allele by various methods known in the art. Methods for determining promoter or enhancer strength include quantitation of the expressed natural protein; insertion of the variant control element into a vector with a reporter gene such as β-galactosidase, luciferase, chloramphenicol acetyltransferase, etc. that provides for convenient quantitation; and the like.

Therapeutic Modalities
Diseases and Conditions
Cancer

In another aspect of the present invention, there is provided a method of treating cancer, a proliferative disease or condition, an immune disorder or a metabolic disorder, by providing a cell, a composition comprising a cell, a factor that regulates a cell, or a composition comprising a factor that regulates a cell, and administering one or more of these to a patient in need of such treatment.

Tumors which can be treated by the methods of the invention include carcinomas, e.g., colon, rectum, prostate, breast, melanoma, ductal, endometrial, stomach, pancreatic, mesothelioma, dysplastic oral mucosa, invasive oral cancer, non-small cell lung carcinoma ("NSCL"), transitional and squamous cell urinary carcinoma, etc.; neurological malignancies, e.g., neuroblastoma, glioblastoma, astrocytoma, gliomas, etc.; hematological malignancies, e.g., childhood acute leukaemia, non-Hodgkin's lymphomas, chronic lymphocytic leukemia, malignant cutaneous T-cells, mycosis fungoides (MF), non-MF cutaneous T-cell lymphoma, lymphomatoid papulosis, T-cell rich cutaneous lymphoid hyperplasia, bullous pemphigoid, discoid lupus erythematosus, lichen planus, etc.; gynecological cancers, e.g., cervical and ovarian; testicular cancers; liver cancers including hepatocellular carcinoma (HCC) and biliary duct tumors; multiple myelomas; tumors of the esophageal tract; other lung tumors including small cell and clear cell; Hodgkin's lymphomas; and sarcomas.

Autoimmune Disease

Autoimmune diseases which are treatable using formulations of the invention include various types of arthritis, such as rheumatoid arthritis and osteoarthritis, various chronic inflammatory conditions of the skin, such as psoriasis, inflammatory bowel disease (IBD), insulin-dependent diabetes, autoimmune diseases such as multiple sclerosis (MS), systemic myasthenia gravis, Graves disease, autoimmune hepatitis, serum sickness, paraneoplastic syndrome, systemic lupus erythematosus (SLE), allergic diseases, transplant rejections, adult respiratory distress syndrome, atherosclerosis, and ischemic diseases due to obstruction of the peripheral vasculature, cardiovasculature, and vasculature of the central nervous system (CNS).

After reading the present disclosure, those skilled in the art will recognize other disease states and/or symptoms which might be prevented, treated and/or mitigated by the administration of formulations of the present invention.

Administration of Therapeutic Nucleic Acids and Polypeptides
Methods of Administration The therapeutic nucleic acids and polypeptides of the invention can be administered in a variety of ways. These include oral, buccal, rectal, parenteral, including intranasal, intramuscular, intravenous, intra-arterial, intraperitoneal, intradermal, transdermal, subcutaneous, intratracheal, intracardiac, intraventricular, intracranial, intrathecal, etc., and administration by implantation. The agents may be administered daily, weekly, or monthly, as appropriate as conventionally determined.

Pharmaceutical Compositions

The therapeutic nucleic acids and polypeptides of the invention can be administered as part of a pharmaceutical composition comprising a subject agent; and a pharmaceutically acceptable excipient. The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

An effective amount of the active agent (e.g., small molecule, antibody specific for a subject polypeptide, or a subject polypeptide) is administered to the host. In some embodiments, the desired result is at least a reduction in a given biological activity of a subject polypeptide as compared to a control. In other embodiments, the desired result is an increase in the level of active subject polypeptide (in the individual, or in a localized anatomical site in the individual), as compared to a control. In further embodiments, the desired result is at least a reduction in enzymatic activity of a subject polypeptide as compared to a control. In yet further embodiments, the desired result is an increase in the level of enzymatically active subject polypeptide (in the individual, or in a localized anatomical site in the individual), as compared to a control.

Typically, the compositions of the instant invention will contain from less than 1% to about 95% of the active ingredient, preferably about 10% to about 50%. Generally, between about 100 mg and 500 mg will be administered to a child and between about 500 mg and 5 grams will be administered to an adult. Administration is generally by injection and often by injection to a localized area. Administration may be performed by stereotactic injection. The frequency of administration will be determined by the care giver based on patient responsiveness. Other effective dosages can be readily determined by one of ordinary skill in the art through routine trials establishing dose response curves.

In order to calculate the amount of subject polypeptide, those skilled in the art could use readily available information with respect to the amount of polypeptide necessary to have a the desired effect. The amount of an agent necessary to increase a level of active subject polypeptide can be calculated from in vitro experimentation. The amount of agent will, of course, vary depending upon the particular agent used.

In the subject methods, the active agent(s) may be administered to the host using any convenient means capable of resulting in the desired effect. Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants, and aerosols.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules, or capsules, for example, with conventional additives, such as lactose, mannitol, corn starch or potato starch; with binders, such as crystalline cellulose, cellulose derivatives, acacia, corn starch, or gelatins; with disintegrators, such as corn starch, potato starch, or sodium carboxymethylcellulose; with lubricants, such as talc or magnesium stearate; and if desired, with diluents, buffering agents, moistening agents, preservatives, and flavoring agents.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art (Gennaro, 2003). The composition or formulation to be administered will, in any event, contain a quantity of the polypeptide adequate to achieve the desired state in the subject being treated.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers, and preservatives.

The agents can be utilized in aerosol formulation to be administered via inhalation. The compounds of the present invention can be formulated into pressurized acceptable propellants such as dichlorodifluoromethane, propane, nitrogen, and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet, or suppository, contains a predetermined amount of the composition containing one or more inhibitors. Similarly, unit dosage forms for injection or intravenous administration may comprise the inhibitor(s) in a composition as a solution in sterile water, normal saline, or another pharmaceutically acceptable carrier.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

The agents of the present invention, including polypeptides, polynucleotides, antibodies, and small molecule modulators, can be used by themselves, with each other, or in combination with pharmaceutically acceptable excipient materials as described above.

Gene Therapy

Gene therapy can be performed in vitro or in vivo. In vivo gene therapy can be accomplished by directly transfecting or transducing a nucleic acid of the invention into the patient's target cells. In vitro gene therapy can be accomplished by transfecting or transducing a nucleic acid of the invention into cells in vitro and then administering them to the patient. Transfection of a nucleic acid of the invention involves its direct introduction into the cell. Transduction of a nucleic acid of the invention involves its introduction into the cell via a vector.

Nucleic acid sequences of the invention can be introduced into tissues or host cells by any number of routes, including viral infection, microinjection, or fusion of vesicles. Both viral and non-viral vectors are suitable for use in the invention. Suitable viral vectors include retroviruses, adenoviruses, herpes viruses, and adeno-associated viruses. Viral vectors can enter cells by receptor-mediated processes and deliver nucleic acids to the cell interior. Non-viral delivery systems suitable for the invention include transfecting plasmids into cells, e.g., by calcium phosphate precipitation and electroporation. Jet injection can provide intramuscular administration (Furth, et al., 1992). The DNA may be coated onto gold microparticle projectiles, and delivered intradermally by a particle bombardment device, or "gene gun" (Tang et al., 1992).

Stem cells provide attractive targets for gene therapy because of their capacity for self renewal and their wide systemic distribution. Correcting a defective gene in a stem cell corrects the defect in the undifferentiated progeny and the differentiated progeny. Because stem cells disseminate throughout the organism, stem cells can be treated in situ or ex vivo, and, post-treatment, travel to their functional site. Sustained expression of transgenes at clinically relevant levels in the progeny of stem cells may provide novel and potentially curative treatments for a wide range of inherited and acquired diseases (Hawley, 2001).

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges can independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a subject polypeptide" includes a plurality of such polypeptides and reference to "the agent" includes reference to one or more agents and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

EXAMPLES

The examples, which are intended to be purely exemplary of the invention and should therefore not be considered to limit the invention in any way, also describe and detail aspects and embodiments of the invention discussed above. The examples are not intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Differential Expression in *E. coli*, Yeast, Plants, Insects, Mammalian Cells, and Cell-Free Systems The sequences of the invention will be expressed in a variety of expression systems. Each expression system will utilize different enzymes to produce different fragments that correspond to various biologically active fragments of the invention.

*E. coli*

Coding sequences will be expressed in *E. coli* by subcloning either the entire coding region, or a selected portion of the coding region into the prokaryotic expression vector pQE16 from Qiagen (Valencia, Calif.). The features of this vector that make it useful for protein expression include: an efficient promoter (phage T5) to drive transcription; expression control provided by the lac operator system, which can be induced by addition of IPTG (isopropyl-beta-D-thiogalactopyranoside), and an encoded 6×His-tag (SEQ ID NO: 14) coding sequence. The latter is a stretch of 6 histidine amino acid residues which can bind very tightly to a nickel atom. The vector can be used to express a recombinant protein with a 6×His-tag (SEQ ID NO: 14) fused to its carboxyl terminus, allowing rapid and efficient purification using Ni-coupled affinity columns.

The entire or the selected partial coding region will be amplified by PCR, then ligated into the digested pQE16 vector. The ligation product will be transformed by electroporation into electrocompetent *E. coli* cells (strain M15[pREP4] from Qiagen), and the transformed cells plated on ampicillin-containing plates. Colonies will be screened for the correct insert in the proper orientation using a PCR reaction employing a gene-specific primer and a vector-specific primer. Positive clones will be sequenced to ensure correct orientation and sequence. To express the proteins, a colony containing a correct recombinant clone will be inoculated into L-Broth containing 100 μg/ml of ampicillin, 25 μg/ml of kanamycin, and the culture grown overnight at 37 degrees C. The saturated culture will be diluted 20-fold in the same medium and allowed to grow to an optical density at 600 nm of 0.5. At this point, IPTG will be added to a final concentration of 1 mM to induce protein expression. The culture will then be grown for an additional 5 hours, and the cells harvested by centrifugation at 3000 times g for 15 minutes.

The resultant pellet will be lysed using a mild, nonionic detergent in 20 mM Tris HCl (pH 7.5) (B PER™ Reagent from Pierce, Rockford, Ill.), or by sonication until the turbid cell suspension turns translucent. The resulting lysate will be further purified using a nickel containing column (Ni-NTA spin column from Qiagen) under non-denaturing conditions. Briefly, the lysate will be adjusted to 300 mM NaCl and 10 mM imidazole then centrifuged at 700 times g through the nickel spin column to allow the His-tagged recombinant protein to bind to the column. The column will be washed twice with wash buffer (50 mM $NaH_2 PO_4$, pH 8.0; 300 mM NaCl; 20 mM imidazole) and eluted with elution buffer (50 mM $NaH_2 PO_4$, pH 8.0; 300 mM NaCl; 250 mM imidazole). All the above procedures will be performed at 4 degrees C. The presence of a purified protein of the predicted size will be confirmed with SDS-PAGE.

Yeast

The sequences of the invention will be expressed in yeast by subcloning either the entire coding region, or a selected portion of the coding region into pENTR/D-TOPO vectors (Invitrogen, Carlsbad, Calif.). The sequences in the pENTR/D-TOPO vectors will be cloned into the yeast expression vector pYES-DEST52 by Gateway LR reaction (Invitrogen, Carlsbad, Calif.). The resulting yeast expression vectors will be transformed into INVSc1 strain from Invitrogen to express the Notch receptor ligands according to the manufacturer's protocol (Invitrogen, Carlsbad Calif.). The expressed polypeptides will have a 6×His-tag (SEQ ID NO: 14) at the C-terminal. Expressed protein will be purified by ProBond™ resin (Invitrogen, Carlsbad, Calif.).

Plants

The sequences of the invention will be expressed in plant cells, e.g., rice, by subcloning either the entire coding region, or a selected portion of the coding region of the membrane proteins supportive of growth into the plant expression vector as described in U.S. Pat. No. 6,127,145. A plasmid transformation vector, p3Dv1.0, will then be constructed with a hygromycin resistance gene, a terminator, a promoter, and a multiple cloning region, as described. Two PCR primers will be used to used to amplify the selected sequences. The N-terminal primer amplifies to a blunt site in frame with the end of p3Dv1.0's signal peptide and the C-terminal primer contains a XhoI site for cloning the fragment into the vector. The vector can be modified so that the plant system utilizes codons optimized to express human proteins.

Insects

The sequences of the invention will be expressed in insect cells by subcloning either the entire coding region, or a selected portion of the coding region of the Notch receptor ligands into pENTR/D-TOPO, which will then be cloned into the Baculovirus expression vector pDEST10 by Gateway LR reaction (Invitrogen, Carlsbad, Calif.). The polypeptides will be expressed by the Bac-to-Bac expression system from Invitrogen (Carlsbad Calif.), briefly described as following. The expression vectors containing the secreted factors will be transformed into competent DH10Bac™ E. coli strain and selected for transposition. The resulting E coli will contain recombinant bacmid that contains the polypeptide of interest. High molecular weight DNA will be isolated from the E. coli containing the recombinant bacmid and then transfected into insect cells with Cellfectin reagent. The expressed polypeptides of interest will have a 6×His-tag (SEQ ID NO: 14) at the N-terminal. Expressed protein will be purified by ProBond™ resin (Invitrogen, Carlsbad, Calif.).

Mammalian Cells

The sequences of the invention will be expressed in mammalian cells by subcloning either the entire coding region, or a selected portion of the coding region into the pENTR vector (Invitrogen) by PCR and transferring it to the mammalian expression vector pDEST12.2 per manufacturer's instructions (Invitrogen). Introduction of the recombinant construct into the host cell will be effected by transfection with Fugene 6 (Roche, Basel, Switzerland) per manufacturer's instructions. A number of types of cells can act as suitable host cells for protein expression. Mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK, and Jurkat cells.

Cell-Free Systems

The sequences of the invention will be expressed in mammalian cells by subcloning either the entire coding region, or a selected portion of the coding region into the appropriate cloning and expression vectors in cell free systems. These can contain the SP6 or T7 promoter for use with prokaryotic and eukaryotic hosts (Sambrook, et al., 1989). These DNA constructs will be used to produce proteins in a rabbit reticulocyte lysate system, in frog oocyte systems, in an E. coli lysate system, or with wheat germ extracts.

Example 2

In Vitro B Cell Development Assay

In vitro B cell development assays were performed to elucidate the function of DLL1sol in hematopoiesis. Human bone marrow (BM) CD34$^+$ hematopoietic stem cells (HSC) (from Cambrex Inc.) were co-cultured with OP9 stromal cells (obtained from Riken Cell Bank) in 24-well tissue culture dishes containing 0.5 ml of DMEM (ATCC) supplemented with 10% heat inactivated Fetal Bovine Serum (ATCC) and 5 ng/ml recombinant human IL-7 (R&D Systems) in a 5% CO$_2$ incubator at 37° C. for 7 days. 5×10$^4$ BM CD34$^+$ cells and OP9 cells were used per well. 50 µl (high dose) or 5 µl (low dose) of DLL1sol protein expressed in Sf9 cells were added to comprise the co-culture. 50 µl of control medium was used as a mock control. After seven days of co-culture, cells were harvested for analysis of B-lineage-specific surface markers by fluorescence activated cell sorting (FACS).

The DLL1sol protein was expressed from cDNA encoding the DLL1sol protein subcloned into a pENTR vector (Invitrogen) according to the manufacturer's instructions. The pENTR DLL1sol was then recombined with BaculoDirect linear DNA (Invitrogen) in a LR reaction according to the manufacturer's instructions. The gene was designed to have no stop codon at the 3' end encoding a C-protein with a C-terminal tag. Sf9 cells (Invitrogen) were transfected in a 6 well plate with the whole LR reaction (20 µl) and cells were selected with 100 µM ganciclovir for 3 days. Supernatant was filtered through a 0.2 µm filter, and used to infect Sf9 cells growing at log phase in 10 cm plates. Cells were again selected for successfully recombined bacmids in Sf9 cells, using 100 µM ganciclovir. After three days of selection, the supernatant was harvested from the 10 cm plate and filtered again. This G2 virus stock was further amplified without selection by infecting a 50 ml suspension culture of Sf9 cells growing at log phase at a concentration of 5×10$^5$ cells/ml. After four days, cells were pelleted and the supernatant sterile-filtered and supplemented with FBS to a final concentration of 10% to provide storage stability. This DLL1sol virus G3 supernatant was stored at 4° C. protected from light. For DLL1sol protein production, a 50 ml suspension culture of High Five™ cells (Invitrogen) growing in log phase at a concentration of 10$^6$ cells/ml was infected with 5 ml virus G3 supernatant and cultured for 3 days. Expression of DLL-1sol-T was confirmed by Western blot using anti V5 epitope monoclonal antibody conjugated to horseradish peroxidase according to the manufacturer's instructions (Invitrogen).

B cell-specific markers were analyzed by FACS analysis. Briefly, cells were lifted from the plates with 1 ml Versene (Gibco BRL), washed with PBS/0.1% BSA (Sigma) and incubated with FITC-conjugated antibody against CD19, a B cell surface marker (BD Biosciences) for 15 minutes at 4° C. After washing, cells were analyzed with a FACS Calibur according to the manufacturer's instructions (Becton Dickinson). B cell differentiation was determined as the percentage of CD19 positive cells in the FACS histogram.

As shown in FIG. 1, the mock-treated co-culture comprised 27.5% CD19$^+$ B cells. In contrast, only 20.9% and 14.8% CD19$^+$ B cells were observed in co-cultures treated with 5 ul and 50 ul of DLL1sol protein, respectively. These results indicate that DLL1sol protein inhibited B cell differentiation and/or proliferation in a dose-dependent manner. Since B cells are important for the pathogenesis of allergic reactions and autoimmune diseases, the inhibition of B cell production by DLL1sol may be beneficial to patients with these diseases. Thus, DLL1sol may be used as a therapeutic agent for allergic reactions and autoimmune diseases, such as asthma, systemic lupus erythematosis (SLE), multiple sclerosis, rheumatoid arthritis, myasthenia gravis, Graves disease, autoimmune hepatitis, serum sickness, and paraneoplastic syndrome. In addition, since DLL1sol inhibited B cell differentiation and/or proliferation, DLL1 may also be used to treat B cell lymphoma.

Example 3

In Vitro T Cell Development Assay

The effect of DLL1sol on T cell development can be evaluated in an in vitro assay using human cord blood CD34$^+$ HSC. CD34$^+$ HSC are co-cultured with OP9 stromal cells in the presence or absence of DLL1sol protein for approximately two weeks. Alternatively, CD34+ HSC are co-cultured with OP9 cells stably infected with a retroviral vector encoding the DLL1sol protein. After incubation for two weeks, CD3 and pre-T alpha mRNA levels are determined by the bDNA assay per manufacturer's instruction (Genospectra, Inc., Fremont, Calif.). The T cell-specific CD3 and pre-T alpha levels can provide a measure of the degree of T cell development.

A PCR product of a DLL1sol in a retroviral vector was amplified using a forward primer (5'-caccatgggcagtcggt-gcgcgctgg-3' (SEQ ID NO: 12) and a reverse primer (5'-ctaccgctctg tgcagtagggcccttc-3' (SEQ ID NO: 13) using DLL1sol cDNA as a template. The PCR product was then sub-cloned into the pENTR/D-TOPO vector per manufacturer's instruction (Invitrogen). The DLL1sol cDNA was transferred to either the pcDNA-DEST40 expression vector (Invitrogen) or the modified retroviral vector pLXIN according to the manufacturer's instructions (BD/Clontech). The resulting DLL1sol retroviral vector was used to transfect the retroviral packaging cell line GP2-293 (BD/Clontech) in a 6-well plate. Approximately 48 hours after transfection, the virus-containing supernatants of transfected GP2-293 cells were collected and used to infect OP9 stromal cells (RIKEN Cell Bank, Japan) according to the Retroviral Gene Transfer and Expression User Manual of BD Biosciences.

To ascertain that DLL1sol protein was expressed from the retroviral vector, conditioned media from GP2-293 cells and OP9 cells transduced with the DLL1sol retroviral vector was collected, centrifuged at low speed to remove cellular debris, and loaded on a 4-12% BisCriterion XT Precast gel (Bio-Rad). Protein expression was analyzed by Western blot analysis with 1:5000 anti-V5/HRP (Invitrogen) and the chemiluminescence detection reagents according to the manufacturer's instruction (Pierce Inc.). As shown in FIG. 2, DLL1 sol protein (indicated by the arrow) was expressed and produced in a soluble form in the DLL1sol retroviral vector-transduced GP2-293 cells and OP9 cells. This indicates that OP9 cells stably transfected with the DLL1sol retroviral vector can be produced for use in T cell development assays.

The experiments described herein can provide a framework for evaluating the use of DLL1sol protein as a promoter of T cell development. As a promoter of T cell development, DLL1sol can be used as a protein therapeutic, for example, to promote T cell regeneration after chemotherapy or radiation treatment in cancer patients.

DLL1sol appears to have both inhibitory and stimulatory properties, such as in inhibiting growth and/or proliferation or differentiation of B cells and in promoting growth, proliferation, and/or differentiation of T cells. Thus, DLL1sol can be applied in therapeutic indications such as treatment of immune disorders, such as autoimmune diseases, or treatment or prophylaxis of infectious diseases.

Example 4

Evaluation of the Effect of DLL1sol on HSC Self-Renewal In Vitro

Bone marrow or cord blood CD34+ HSCs are cultured in the absence or presence of DLL1sol protein, and the number of CD34+ cells are measured intermittently from three days to three weeks following the addition of DLL1sol. DLL1sol that promotes the expansion of HSCs in vitro can be used as a therapeutic such as for ex vivo production of HSC for bone marrow transplantation, or for in vivo hematopoietic cell regeneration after chemotherapy or radiation in cancer patients.

Example 5

Investigation of the In Vivo Functions of DLL1sol

To examine the effect of DLL1sol on T/B cell hematopoiesis in vivo, DLL1sol protein is administered intravenously into mice approximately twice per week. In addition, ESpresso mice (PCT/US04/11270) overexpressing DLL1sol can be generated for the evaluation of DLL1sol's role in hematopoiesis. The effects of DLL1sol on T and B cell development are analyzed by FACS with antibodies directed against the T cell specific markers CD4, CD8, and CD3, and the B cell specific markers B220. The effect of DLL1sol protein on Th1 and Th2 cells is analyzed by monitoring the secretion of IFN-gamma (secreted by Th1 cells) and IL-4 (secreted by Th2 cells).

Example 6

Effect of DLL1sol on Th1 and Th2 CD4 T Helper Cell Differentiation

Recently, Amsen et al., 2004 compared the Notch ligand families Delta and Jagged, and demonstrated that Delta induces Th1 cell differentiation, while Jagged induces Th2 cell differentiation. The present invention provides a method to evaluate the effect of Dll1sol on Th1 and Th2 cell differentiation using the methods described by Amsen et al., 2004, in the presence of DLL1sol protein. The DLL1sol proteins of the invention may function as an agonist or an antagonist of Th1 cell differentiation, and/or as an agonist or an antagonist of Th2 cell differentiation. Based on the results obtained in the experiments described in the previous Examples, a DLL1sol protein that functions as an antagonist for Th1 differentiation can be used in the prophylaxis and treatment of Th1-mediated autoimmune diseases, such as multiple sclerosis and rheumatoid arthritis. A DLL1sol protein that functions as an agonist for Th1 differentiation can be used to change the Th1/Th2 balance, and thus may provide prophylaxis and treatment for Th2-mediated diseases, such as asthma.

REFERENCES

The specification is most thoroughly understood in light of the cited references, all of which are hereby incorporated by reference in their entireties. The disclosures of the patents, applications, and other references cited above are also herein incorporated by reference in their entireties. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which, may need to be independently confirmed.

Amsen, D., Blander, J. M., Lee, G. R., Tanigaki, K., Honjo, T., Flavell, R. A. (2004) Instruction of distinct CD4 T helper cell fates by different notch ligands on antigen-presenting cells. *Cell* 117:515-526.

Apelqvist, A. et al., "Notch signaling controls pancreatic cell differentiation." Nature 400: 877-881 (1999).

Ausubel, F., Brent. R., Kingston, R. E., Moore, D. D., Seidman, J. G., Smith, J. A., eds. (1999) Short Protocols in Molecular Biology. 4th ed., Wiley & Sons.

Ballance, D. J., Buxton, F. P., Turner, G. (1983) Transformation of *Aspergillus nidulans* by the orotidine-5'-phosphate decarboxylase gene of *Neurospora crassa. Biochem. Biophys. Res. Commun.* 112:284-289.

Barany, F. (1985) Single-stranded hexameric linkers: a system for in-phase insertion mutagenesis and protein engineering. *Gene* 37:111-123.

Barnes, D., Sato, G. (1980) Methods for growth of cultured cells in serum-free medium. *Anal. Biochem.* 102:255-270.

Barton, M. C., Hoekstra, M. F., Emerson, B. M. (1990) Site-directed, recombination-mediated mutagenesis of a complex gene locus. *Nucleic Acids Res.* 18:7349-7355.

Bashkin, J. K., Sampath, U., Frolova, E. (1995) Ribozyme mimics as catalytic antisense reagents. *Appl. Biochem. Biotechnol.* 54:43-56.

Beach, D., Durkacz, B., Nurse, P. (1982) Functionally homologous cell cycle control genes in budding and fission yeast. *Nature* 300:706-709.

Beigelman, L., Karpeisky, A., Matulic-Adamic, J., Haeberli, P., Sweedler, D., Usman, N. (1995) Synthesis of 2'-modified nucleotides and their incorporation into hammerhead ribozymes. *Nucleic Acids Res.* 23:4434-4442.

Boshart, M., Weber, F., Jahn, G., Dorsch-Hasler, K., Fleckenstein, B., Schaffner, W. (1985) A very strong enhancer is located upstream of an immediate early gene of human cytomegalovirus. *Cell* 41:521-530.

Carbonell, L. F., Hodge, M. R., Tomalski, M. D., Miller, L. K. (1988) Synthesis of a gene coding for an insect-specific scorpion neurotoxin and attempts to express it using baculovirus vectors. *Gene* 73:409-418.

Chakravarty, A. (1999) Population genetics—making sense out of sequence. *Nature Genetics* 21:56-60.

Chalifour, L. E., Fahmy, R., Holder, E. L., Hutchinson, E. W., Osterland, C. K., Schipper, H. M., Wang, E. (1994) A method for analysis of gene expression patterns. *Anal. Biochem.* 216: 299-304.

Chang, A. C., Nunberg, J. H., Kaufman, R T, Erlich, H. A., Schimke, R. T., Cohen, S. N. (1978). Phenotypic expression in *E. coli* of a DNA sequence coding for mouse dihydrofolate reductase. *Nature* 275:617-624.

Colicelli, J., Lobel, L. I., Goff, S. P. (1985) A temperature-sensitive mutation constructed by "linker insertion" mutagenesis. *Mol. Gen. Genet.* 199:537-539.

Cregg, J. M., Barringer, K. J., Hessler, A. Y., Madden, K. R. (1985) *Pichia pastoris* as a host system for transformations. *Mol. Cell. Biol.* 5:3376-3385.

Das, S., Kellermann, E., Hollenberg, C. P. (1984) Transformation of *Kluyveromyces fragilis. J. Bacteriol.* 158:1165-1167.

Davidow, L. S., Kaczmarek, F. S., DeZeeuw, J. R., Conlon, S. W., Lauth, M. R., Pereira, D. A., Franke, A. E. (1987) The *Yarrowia lipolytica* LEU2 gene. *Curr. Genet.* 11:377-383.

de Boer, H. A., Comstock, L. J., Vasser, M. (1993) The tac promoter: a functional hybrid derived from the trp and lac promoters. *Proc. Natl. Acad. Sci.* (USA) 80:21-25.

de la Pompa, J. L. et al., "Conservation of the Notch signaling pathway in mammalian neurogenesis," Development 124 (6): 1139-48 (1997).

De Louvencourt, L., Fukuhara, H., Heslot, H., Wesolowski, M. (1983) Transformation of *Kluyveromyces lactis* by killer plasmid DNA. *J. Bacteriol.* 154:737-742.

Deasy, B. M., Huard, J. (2002) Gene therapy and tissue engineering based on muscle-derived stem cells. Curr. Opin. Mol. Ther. 4:382-389.

Delahunty, C., Ankener, W., Deng, Q., Eng, J., Nickerson, D. A. (1996) Testing the feasibility of DNA typing for human identification by PCR and an oligonucleotide ligation assay. *Am. J. Human Genetics* 58:1239-1246.

Deutscher, M. P., Simon, M. I., Abelson, J. N., eds. (1990) *Guide to Protein Purification: Methods in Enzymology.* (*Methods in Enzymology Series, Vol* 182). Academic Press.

Dieffenbach, C. W., Dveksler, G. S., eds. (1995) *PCR Primer: A Laboratory Manual*. Cold Spring Harbor Laboratory Press.

Dijkema, R., van der Meide, P. H., Pouwels, P. H., Caspers, M., Dubbeld, M., Schellekens, H. (1985) Cloning and expression of the chromosomal immune interferon gene of the rat. *EMBO J.* 4:761-767.

Doerfler, W., Bohm, P., eds. (1987) *The Molecular Biology Of Baculoviruses*. Springer-Verlag, Inc.

Egilsson, V., Gudnason, V., Jonasdottir, A., Ingvarsson, S., Andresdottir, V. (1986) Catabolite repressive effects of 5-thio-D-glucose on *Saccharomyces cerevisiae. J. Gen. Microbiol.* 132:3309-3313.

Fanning, A. S., Anderson, J. M. (1999) PDZ domains: fundamental building blocks in the organization of protein complexes at the plasma membrane. *J. Clin. Invest.* 103:767-772.

Furth, P. A., Shamay, A., Wall, R. J., Hennighausen, L. (1992) Gene transfer into somatic tissues by jet injection. *Anal Biochem.* 205:365-368.

Gaillardin, C., Ribet, A. M. (1987) LEU2 directed expression of beta-galactosidase activity and phleomycin resistance in *Yarrowia lipolytica. Curr. Genet.* 11:369-375.

Gaudilliere, B., Shi, Y., Bormi, A. (2002) RNA interference reveals a requirement for MEF2A in activity-dependent neuronal survival. *J. Biol. Chem.* 277:46,442-46,446 [epub Sep. 13, 2002, ahead of print].

Gennaro, A. R. (2003) *Remington: The Science and Practice of Pharmacy with Facts and Comparisons: DrugfactsPlus*. 20th ed. Lippincott Williams & Williams.

Goeddel, D. V., Heyneker, H. L., Hozumi, T., Arentzen, R., Itakura, K., Yansura, D. G., Ross, M. J., Mizzari, G., Crea, R., Seeburg, P. H. (1979) Direct expression in *E. coli* of a DNA sequence coding for human growth hormone. *Nature* 281:544-548.

Goeddel, D. V., Shephard, H. M., Yelverton, E., Leung, D., Crea, R., Sloma, A., Pestka, S. (1980) Synthesis of human fibroblast interferon by *E. coli. Nucleic Acids Res.* 8:4057-4074.

Gorman, C. M., Merlino, G. T., Willingham, M. C., Pastan, I., Howard, B. H. (1982) The Rous sarcoma virus long terminal repeat is a strong promoter when introduced into a variety of eucaryotic cells by DNA-mediated transfection. *Proc. Natl. Acad. Sci.* (USA) 79:6777-6781.

Grandbarbe, L. et al., "Delta-Notch signaling controls the generation of neurons/glia from neural stem cells in a stepwise process." Development 130(7): 1391-1402 (2003).

Gustin, K., Burk, R. D. (1993) A rapid method for generating linker scanning mutants utilizing PCR. *Biotechniques* 14:22-24.

Ham, R. G., McKeehan, W. L. (1979) Media and growth requirements. *Methods Enzymol.* 58:44-93.

Han, W. and Moore, M. A. S., "A soluble form of human Delta-like-1 inhibits differentiation of hematopoietic progenitor cells." Blood 95(5): 1616-1625 (2000).

Harlow, E., Lane, D., eds. (1988) *Antibodies: A Laboratory Manual*. Cold Spring Harbor Laboratory Press.

Harlow, E., Lane, D., Harlow, E., eds. (1998) *Using Antibodies: A Laboratory Manual: Portable Protocol NO. 1*. Cold Spring Harbor Laboratory Press.

Harris, J. M., Martin, N. E., Modi, M. (2001) Pegylation: a novel process for modifying pharmacokinetics. *Clin. Pharmacokinet.* 40:539-551.

Hawley, R. G. (2001) Progress toward vector design for hematopoeitic stem cell gene therapy. *Curr. Gene Ther.* 1:1-17.

Heissig, B., Hattori, K., Dias, S., Friedrich, M., Ferris, B., Hackett, N. R., Crystal, R. G., Besmer, P., Lyden, D., Moore, M. A., Werb, Z., Rafii, S. (2002) Recruitment of stem and progenitor cells from the bone marrow niche requires MMP-9 mediated release of kit-ligand. *Cell* 109: 625-637.

Henningson, C. T. Jr., Stanislaus, M. A., Gewirtz, A. M. (2003) 28. Embryonic and adult stem cell therapy. *J. Allergy Clin. Immunol.* 111:S745-S753.

Hinnen, A., Hicks, J. B., Fink, G. R. (1978) Transformation of yeast. *Proc. Natl. Acad. Sci.* (USA) 75:1929-1933.

Hong, G. F. (1982) Sequencing of large double-stranded DNA using the dideoxy sequencing technique. *Biosci. Rep.* 2:907-912.

Hooper, M. L. (1993) *Embryonal Stem Cells: Introducing Planned Changes into the Animal Germline* Gordon & Breach Science Pub.

Ito, H., Fukuda, Y., Murata, K., Kimura, A. (1978) Transformation of intact yeast cells treated with alkali cations. *J. Bacteriol.* 153:163-168.

Jones, D. H., Winistorfer, S. C. (1992) Recombinant circle PCR and recombination PCR for site-specific mutagenesis without PCR product purification. *Biotechniques* 12:528-530.

Jones, P., ed. (1998a) *Vectors: Cloning Applications: Essential Techniques*, John Wiley & Son, Ltd.

Jones, P., ed. (1998b) *Vectors: Expression Systems: Essential Techniques*, John Wiley & Son, Ltd.

Kelly, J. M., Hynes, M. J. (1985) Transformation of *Aspergillus niger* by the mdS gene of *Aspergillus nidulans*. *EMBO J.* 4:475-479.

Keown, W. A., Campbell, C. R., Kucherlapati, R. S. (1990) Methods for introducing DNA into mammalian cells. *Methods Enzymol.* 185:527-537.

Kolonin, M. G., Finley, R. L. Jr. (1998) Targeting cyclin-dependent kinases in *Drosophila* with peptide aptamers. *Proc. Natl. Acad. Sci.* (USA) 95:14,266-14,271.

Kunze, G. et al., (1985) Transformation of the industrially important yeasts *Candida maltosa* and *Pichia* guilliermondii. *J Basic Microbiol.* 25:141-144.

Kurtz, M. B., Cortelyou, M. W., Kirsch, D. R. (1986) Integrative transformation of *Candida albicans*, using a cloned *Candida* ADE2 gene. *Mol. Cell. Biol.* 6:142-149.

Lebacq-Verheyden, A. M., Kasprzyk, P. G., Raum, M. G., Van Wyke Coelingh, K., Lebacq, J. A., Battey, J. F. (1988) Posttranslational processing of endogenous and of baculovirus-expressed human gastrin-releasing peptide precursor. *Mol. Cell. Biol.* 8:3129-3135.

Luckow, V., Summers, M. (1988) Trends in the development of baculovirus expression vectors. *Bio/Technology* 6:47-55.

Maeda, S., Kawai, T., Obinata, M., Fujiwara, H., Horiuchi, T., Saeki, Y., Sato, Y., Furusawa, M. (1985) Production of human alpha-interferon in silkworm using a baculovirus vector. *Nature* 315:592-594.

Marotti, K. R., Tomich, C. S. (1989) Simple and efficient oligonucleotide-directed mutagenesis using one primer and circular plasmid DNA template. (1989) *Gene Anal. Tech.* 6:67-70.

Martin, B. M., Tsuji, S., LaMarca, M. E., Maysak, K., Eliason, W., Ginns, E. I. (1988) Glycosylation and processing of high levels of active human glucocerebrosidase in invertebrate cells using a baculovirus expression vector. *DNA* 7:99-106.

McGraw, R. A. III (1984) Dideoxy DNA sequencing with end-labeled oligonucleotide primers. *Anal. Biochem.* 143: 298-303.

McPherson, M. J., Møller, S. G., Benyon, R., Howe, C. (2000) *PCR Basics: From Background to Bench*. Springer Verlag.

Miller, L. K. (1988) Baculoviruses as gene expression vectors. *Ann. Rev. Microbiol.* 42:177-199.

Milligan, J. F., Matteucci, M. D., Martin, J. C. (1993) Current concepts in antisense drug design. *J. Med. Chem.* 36:1923-1937.

Miyajima, A., Schreurs, J., Otsu, K., Kondo, A., Arai, K., Maeda, S. (1987) Use of the silkworm, *Bombyx mori*, and an insect baculovirus vector for high-level expression and secretion of biologically active mouse interleukin-3. *Gene* 58:273-281.

Molineux G. (2002) Pegylation: engineering improved pharmaceuticals for enhanced therapy. *Cancer Treat. Rev.* 28 Suppl A:13-16.

Nagase, T., Nakayama, M., Nakajima, D., Kikuno, R., Ohara, O. (2001) Prediction of the coding sequences of unidentified human genes. XX. The complete sequences of 100 new cDNA clones from brain which code for large proteins in vitro. *DNA Res.* 8:85-95.

O'Neil, N. J., Martin, R. L., Tomlinson, M. L., Jones, M. R., Coulson, A., Kuwabara, P. E. (2001) RNA-mediated interference as a tool for identifying drug targets. *Am. J. Pharmacogenomics* 1:45-53.

Pietu, G., Alibert, O., Guichard, V., Lamy, B., Bois, F., Mariage-Sampson, R., Hougatte, R., Soularue, P., Auffray, C. (1996) Novel gene transcripts preferentially expressed in human muscles revealed by quantitative hybridization of a high density cDNA array. *Genome Res.* 6:492-503.

Pinkert, C. A., ed. (1994) *Transgenic Animal Technology: A Laboratory Handbook*. Academic Press.

Post, L. C., et al., "Notch/Delta expression in the developing mouse lung." Mech. Dev. 98 (1-2): 95-98 (2000).

Prentki, P., Krisch, H. M. (1984) In vitro insertional mutagenesis with a selectable DNA fragment. *Gene* 29:303-313.

Pui, J. C., Allman, D., Xu, L., DeRocco, S., Karnell, F. G., Bakkour, S., Lee, J. Y., Kadesch, T., Hardy, R. R., Aster, J. C., Pear, W. S. (1999) Notch1 expression in early lymphopoiesis influences B versus T lineage determination. *Immunity* 11299-308.

Radtke, F., Wilson, A., Stark, G., Bauer, M., van Meerwijk, J., MacDonald, H. R., Aguet, M. (1999) Deficient T cell fate specification in mice with an induced inactivation of Notch1. *Immunity* 10:547-558.

Raval, P. (1994) Qualitative and quantitative determination of mRNA. *J. Pharmacol. Toxicol. Methods* 32:125-127.

Riley, J., Butler, R., Ogilvie, D., Finniear, R., Jenner D., Powell, S., Anand, R., Smith, J. C., Markham, A. F. (1990) A novel, rapid method for the isolation of terminal sequences from yeast artificial chromosome (YAC) clones. *Nuc. Acids Res.* 18:2887-2890.

Roggenkamp, R., Janowicz, Z., Stanikowski, B., Hollenberg, C. P. (1984) Biosynthesis and regulation of the peroxisomal methanol oxidase from the methylotrophic yeast *Hansenula polymorpha*. *Mol. Gen. Genet.* 194:489-493.

Saiki, R. K, Gelfand, D. H., Stoffel, S., Scharf, S. J., Higuchi, R., Horn, G. T., Mullis, K. B., Erlich, H. A. (1988) Primer-directed enzymatic amplification of DNA with amplification of DNA with a thermostable DNA polymerase. *Science* 239:487-91.

Sambrook, J., Russell, D. W., Sambrook, J. (1989) *Molecular Cloning, A Laboratory Manual*. $2^{nd}$ ed., Cold Spring Harbor Laboratory Press.

Sayers, J. R., Krekel, C., Eckstein, F. (1992) Rapid high-efficiency site-directed mutagenesis by the phosphothioate approach. *Biotechniques* 13:592-596.

Schmitt, T. M., Zuniga-Pflucker, J. C. (2002) Induction of T cell development from hematopoietic progenitor cells by delta-like-1 in vitro. *Immunity* 17:749-756.

Setlow, J., Hollaender, A. eds. (1986) *Genetic Engineering: Principles and Methods.* Plenum Pub. Corp.

Siebenlist, U., Simpson, R. B., Gilbert, W. (1980) *E. coli* RNA polymerase interacts homologously with two different promoters. *Cell* 20:269-281.

Singh, N. et al., "Expression of notch receptors, notch ligands, and fringe genes in hematopoiesis." Exp. Hematol. 28(5): 527-534 (2000).

Six, E. et al., "The Notch ligand Delta1 is sequentially cleaved by an ADAM protease and γ-secretase." Proc. Natl. Acad. Sci. USA 100(13): 7638-7643 (2003).

Slavin, S., Or, R., Aker, M., Shapira, M. Y., Panigrahi, S., Symeonidis, A., Cividalli, G., Nagler, A. (2001) Nonmyeloablative stem cell transplantation for the treatment of cancer and life-threatening nonmalignant disorders: past accomplishments and future goals. *Cancer Chemother. Pharmacol.* 48 Suppl 1:S79-84.

Smith, G. E., Ju, G., Ericson, B. L., Moschera, J., Lahm, H. W., Chizzonite, R., Summers, M. D. (1985) Modification and secretion of human interleukin 2 produced in insect cells by a baculovirus expression vector. *Proc. Natl. Acad. Sci.* (USA) 82:8404-8408.

Soares, M. B. (1997) Identification and cloning of differentially expressed genes. *Curr. Opin. Biotechnol.* 8:542-546.

Stolz, L. E., Tuan, R. S. (1996) Hybridization of biotinylated oligo(dT) for eukaryotic mRNA quantitation. *Mol. Biotechnol.* 6:225-230.

Strünkelnberg, M., Bonengel, B., Moda, L. M., Hertenstein, A., de Couet, H. G., Ramos, R. G., Fischbach, K. F. (2001) rst and its paralogue kirre act redundantly during embryonic muscle development in *Drosophila. Development* 128:4229-4239.

Tang, D. C., DeVit, M., Johnston, S. A. (1992) Genetic immunization is a simple method for eliciting an immune response. *Nature* 356:152-154.

Tezuka, K. et al., "Stimulation of osteoblastic cell differentiation by Notch." J. Bone Miner Res. 17(2): 231-239 (2002).

Tilburn, J., Scazzocchio, C., Taylor, G. G., Zabicky-Zissman, J. H., Lockington, R. A., Davies, R. W. (1983) Transformation by integration in *Aspergillus nidulans. Gene* 26:205-221.

Trounson, A. (2002) Human embryonic stem cells: mother of all cell and tissue types. *Reprod. Biomed. Online* 4 Suppl 1:58-63.

Ueno, H., Sakita-Ishikawa, M., Morikawa, Y., Nakano, T., Kitamura, T., Saito, M. (2003) A stromal cell-derived membrane protein that supports hematopoeitic stem cells. *Nat. Immunol.* 4:457-463.

van den Berg, J. A., van der Laken, K. J., van Ooyen, A. J., Renniers, T. C., Rietveld, K., Schaap, A., Brake, A. J., Bishop, R. J., Schultz, K., Moyer, D. (1990) *Kluyveromyces* as a host for heterologous gene expression: expression and secretion of prochymosin. *Bio/Technology* 8:135-139.

Van Laar, J. M., Tyndall, A. (2003) Intense immunosuppression and stem-cell transplantation for patients with severe rheumatic autoimmune disease: a review. *Cancer Control* 10:57-65.

Vlak, J. M., Klinkenberg, F. A., Zaal, K. J., Usmany, M., Klinge-Roode, E. C., Geervliet, J. B., Roosien, J., van Lent, J. W. (1988) Functional studies on the p10 gene of *Autographa californica* nuclear polyhedrosis virus using a recombinant expressing a p10-beta-galactosidase fusion gene. *J. Gen. Virol.* 69:765-776.

Wagner, R. W., Matteucci, M. D., Grant, D., Huang, T., Froehler, B. C. (1996) Potent and selective inhibition of gene expression by an antisense heptanucleotide. *Nat. Biotechnol.* 14:840-844.

Wagner, R. W., Matteucci, M. D., Lewis, J. G., Gutierrez, A. J., Moulds, C., Froehler, B. C. (1993) Antisense gene inhibition by oligonucleotides containing C-5 propyne pyrimidines. *Science* 260:1510-1513.

Weiner, M. P., Felts, K. A., Simcox, T. G., Braman, J. C. (1993) A method for the site-directed mono- and multi-mutagenesis of double-stranded DNA. *Gene* 126:35-41.

Weissman, I. L. (2000) Translating stem and progenitor cell biology to the clinic: barriers and opportunities. *Science* 287:1442-1446.

Weng, S., Gu, K., Hammond, P. W., Lohse, P., Rise, C., Wagner, R. W., Wright, M. C., Kuimelis, R. G. (2002) Generating addressable protein microarrays with PROfusion covalent mRNA-protein fusion technology. *Proteomics* 2:48-57.

Winssinger, N., Ficarro, S., Schultz, P. G., and Harris, J. L. (2002) Profiling protein function with small molecule microarrays. *Proc. Natl. Acad. Sci.* (USA) 99:11,139-11,144.

Xu, C. W., Mendelsohn, A. R., Brent, R. (1997) Cells that register logical relationships among proteins. *Proc. Natl. Acad. Sci.* (USA) 94:12,473-12,478.

Yelton, M. M., Hamer, J. E., Timberlake, W. E. (1984) Transformation of *Aspergillus nidulans* by using a trpC plasmid. *Proc. Natl. Acad. Sci.* (USA) 81:1470-1474.

Zallipsky, S. (1995) Functionalized poly(ethylene glycols) for preparation of biologically relevant conjugates. *Bioconjugate Chem.,* 6:150-165.

Zhao, N., Hashida, H., Takhshi, N., Misumi, Y., Sakaki, Y. (1995) High-density cDNA filter analysis: a novel approach for large-scale quantitative analysis of gene expression. *Gene* 156:207-215.

Zhu, D. L. (1989) Oligonucleotide-directed cleavage and repair of a single stranded vector: a method of site-specific mutagenesis. *Anal. Biochem.* 177:120-124.

TABLE 1

Structural Characteristics of SEQ ID NO: 3 Compared to Known DLL1

| Source ID | Classification | Pred. Protein Length | Tree vote | Signal Peptide Coords. | Mature Protein Coords. | Alternate Signal Peptide Coords. | Alternate Mature Protein Coords. | Hydrophobicity Coords. | TM Coords. | TM | Non-TM Coords. |
|---|---|---|---|---|---|---|---|---|---|---|---|
| Dll1sol | | 224 | 1 | (1-21) | (22-224) | (6-18) | (19-225) | (9-21) | 1-224 | 0 | (1-224) |
| | | | | | | (5-17) | (18-225) | | | | |
| | | | | | | (9-21) | (22-225) | | | | |

TABLE 1-continued

Structural Characteristics of SEQ ID NO: 3 Compared to Known DLL1

| Source ID | Classification | Pred. Protein Length | Tree vote | Signal Peptide Coords. | Mature Protein Coords. | Alternate Signal Peptide Coords. | Alternate Mature Protein Coords. | Hydro-phobicity Coords. | TM Coords. | TM | Non-TM Coords. |
|---|---|---|---|---|---|---|---|---|---|---|---|
| NP_005609: NM_005618 | STM Type I membrane | 723 | 0 | (1-21) | (22-723) | (6-18) (5-17) (9-21) | (19-724) (18-724) (22-724) | (9-21) | (1-544) (568-567) | 1 | (1-544) (568-723) |

TABLE 2

Pfam Coordinates

| FP ID | Source ID | Pfam | Coordinates |
|---|---|---|---|
| HG1018160 | Dll1sol | DSL | (159-221) |
| HG1018165 | NP_005609:NM_005618 | DSL | (159-221) |
| HG1018165 | NP_005609:NM_005618 | EGF | (409-440) |
| HG1018165 | NP_005609:NM_005618 | EGF | (447-478) |
| HG1018165 | NP_005609:NM_005618 | EGF | (332-363) |
| HG1018165 | NP_005609:NM_005618 | EGF | (292-325) |
| HG1018165 | NP_005609:NM_005618 | EGF | (370-402) |
| HG1018165 | NP_005609:NM_005618 | EGF | (485-516) |

TABLE 3

Top Human Hit

| FP ID | Source ID | Top Human Hit Accession ID | Top Human Hit Annotaion | Top Human Hit Length | Number of Matches | % ID over Query Length | % ID over Human Hit Length |
|---|---|---|---|---|---|---|---|
| HG1018160 | Dll1sol | gi13121982lsplO00548lDLL1_HUMAN | Delta-like protein 1 precursor (Drosophila Delta homolog 1) (Delta 1) (H-Delta-1) (UNQ146/PRO172) | 723 | 223 | 100 | 31 |
| HG1018165 | NP_005609: NM_005618 | gi110518497lreflNP_005609.2l | delta-like 1; delta-like 1 protein; delta (Drosophila)-like 1 [Homo sapiens] | 723 | 723 | 100 | 100 |

The invention claimed is:

1. An isolated polypeptide, wherein the amino acid sequence consists of SEQ ID NO: 3, SEQ ID NO: 4, SEQ ID NO: 5, or SEQ ID NO: 6.

2. The polypeptide of claim 1 wherein the amino acid sequence consists of SEQ ID NO: 3.

3. The polypeptide of claim 1 wherein the amino acid sequence consists of SEQ ID NO: 4.

4. The polypeptide of claim 1 wherein the amino acid sequence consists of SEQ ID NO: 5.

5. The polypeptide of claim 1 wherein the amino acid sequence consists SEQ ID NO: 6.

6. An isolated polypeptide wherein the amino acid sequence consists of amino acids x to 224 of SEQ ID NO: 3, and wherein x is any one of amino acids 18 to 158.

7. A molecule comprising:
a polypeptide, wherein the polypeptide amino acid sequence consists of SEQ ID NO: 3, SEQ ID NO: 4, SEQ ID NO: 5, SEQ ID NO: 6, or amino acids x to 224 of SEQ ID NO: 3 wherein x is any one of amino acids 18 to 158, fused to at least one fusion partner.

8. The molecule of claim 7, wherein the fusion partner is albumin.

9. The molecule of claim 7, wherein the fusion partner is polyethylene glycol.

10. The molecule of claim 7, wherein the polypeptide amino acid sequence consists of SEQ ID NO: 3.

11. The molecule of claim 7, wherein the polypeptide amino acid sequence consists of SEQ ID NO: 4.

12. The molecule of claim 7, wherein the polypeptide amino acid sequence consists of SEQ ID NO: 5.

13. The molecule of claim 7, wherein the polypeptide amino acid sequence consists of SEQ ID NO: 6.

14. The molecule of claim 7, wherein the polypeptide amino acid sequence consists of amino acids x to 224 of SEQ ID NO: 3 wherein x is any one of amino acids 18 to 158.

* * * * *

```
                        SEQUENCE LISTING

<160> NUMBER OF SEQ ID NOS: 14

<210> SEQ ID NO 1
<211> LENGTH: 675
<212> TYPE: DNA
<213> ORGANISM: Homo sapiens

<400> SEQUENCE: 1
atgggcagtc ggtgcgcgct ggccctggcg gtgctctcgg ccttgctgtg tcaggtctgg      60
agctctgggg tgttcgaact gaagctgcag gagttcgtca acaagaaggg gctgctgggg     120
aaccgcaact gctgccgcgg gggcgcgggg ccaccgcgt gcgcctgccg gaccttcttc     180
cgcgtgtgcc tcaagcacta ccaggccagc gtgtccccg agccgccctg cacctacggc     240
agcgccgtca ccccgtgct gggcgtcgac tccttcagtc tgcccgacgg cggggcgcc     300 gactccgcgt tcagcaaccc catccgcttc ccttcggct tcacctggcc gggcaccttc     360
tctctgatta ttgaagctct ccacacagat tctcctgatg acctcgcaac agaaaaccca     420
gaaagactca tcagccgcct ggccacccag aggcacctga cggtgggcga ggagtggtcc     480
```

```
caggacctgc acagcagcgg ccgcacggac ctcaagtact cctaccgctt cgtgtgtgac      540
gaacactact acggagaggg ctgctccgtt ttctgccgtc cccgggacga tgccttcggc      600
cacttcacct gtggggagcg tggggagaaa gtgtgcaacc ctggctggaa agggccctac      660
tgcacagagc ggtag                                                      675

<210> SEQ ID NO 2
<211> LENGTH: 2172
<212> TYPE: DNA
<213> ORGANISM: Homo sapiens

<400> SEQUENCE: 2
atgggcagtc ggtgcgcgct ggccctggcg gtgctctcgg ccttgctgtg tcaggtctgg       60
agctctgggg tgttcgaact gaagctgcag gagttcgtca caagaaggg gctgctgggg      120 aaccgcaact gctgccgcgg gggcgcgggg ccaccgccgt gcgcctgccg gaccttcttc      180
cgcgtgtgcc tcaagcacta ccaggccagc gtgtccccg agccgcctg cacctacggc       240 agcgccgtca cccccgtgct gggcgtcgac tccttcagtc tgcccgacgg cggggcgcc       300 gactccgcgt tcagcaaccc catccgcttc cccttcggct tcacctggcc gggcaccttc      360
tctctgatta ttgaagctct ccacacagat tctcctgatg acctcgcaac agaaaaccca      420
gaaagactca tcagccgcct ggccacccag aggcacctga cggtgggcga ggagtggtcc      480
caggacctgc acagcagcgg ccgcacggac ctcaagtact cctaccgctt cgtgtgtgac      540
gaacactact acggagaggg ctgctccgtt ttctgccgtc cccgggacga tgccttcggc      600
cacttcacct gtggggagcg tggggagaaa gtgtgcaacc ctggctggaa agggccctac      660
tgcacagagc cgatctgcct gcctggatgt gatgagcagc atggattttg tgacaaacca      720
ggggaatgca agtgcagagt gggctggcag ggccggtact gtgacgagtg tatccgctat      780
ccaggctgtc tccatggcac ctgccagcag ccctggcagt gcaactgcca ggaaggctgg      840
gggggccttt tctgcaacca ggacctgaac tactgcacac accataagcc ctgcaagaat      900
ggagccacct gcaccaacac gggccagggg agctacactt gctcttgccg gcctgggtac      960
acaggtgcca cctgcgagct ggggattgac gagtgtgacc ccagcccttg taagaacgga     1020
gggagctgca cggatctcga gaacagctac tcctgtacct gcccacccgg cttctacggc     1080
aaaatctgtg aattgagtgc catgacctgt gcggacggcc cttgctttaa cggggggtcgg     1140 tgctcagaca gccccgatgg agggtacagc tgccgctgcc ccgtgggcta ctccggcttc     1200
aactgtgaga agaaaattga ctactgcagc tcttcaccct gttctaatgg tgccaagtgt     1260
gtggacctcg gtgatgccta cctgtgccgc tgccaggccg gcttctcggg gaggcactgt     1320
gacgacaacg tggacgactg cgcctcctcc ccgtgcgcca acggggcac ctgccgggat     1380 ggcgtgaacg acttctcctg cacctgcccg cctggctaca cggcaggaa ctgcagtgcc     1440 cccgtcagca ggtgcgagca cgcaccctgc cacaatgggg ccacctgcca ccagaggggc     1500
cacggctatg tgtgcgaatg tgcccgaagc tacgggggtc ccaactgcca gttcctgctc     1560
cccgagctgc ccccgggccc agcggtggtg gacctcactg agaagctaga gggccagggc     1620
gggccattcc cctgggtggc cgtgtgcgcc ggggtcatcc ttgtcctcat gctgctgctg     1680
ggctgtgccg ctgtggtggt ctgcgtccgg ctgaggctgc agaagcaccg gccccagcc     1740 gacccctgcc gggggggagac ggagaccatg aacaacctgg ccaactgcca gcgtgagaag     1800
gacatctcag tcagcatcat cggggccacg cagatcaaga acaccaacaa gaaggcggac     1860
```

-continued

```
ttccacgggg accacagcgc cgacaagaat ggcttcaagg cccgctaccc agcggtggac    1920
tataacctcg tgcaggacct caagggtgac gacaccgccg tcagggacgc gcacagcaag    1980
cgtgacacca agtgccagcc ccagggctcc tcagggagg agaagggac cccgaccaca      2040 ctcagggtg gagaagcatc tgaaagaaaa aggccggact cgggctgttc aacttcaaaa     2100
gacaccaagt accagtcggt gtacgtcata tccgaggaga aggatgagtg cgtcatagca    2160
actgaggtgt aa                                                        2172
```

<210> SEQ ID NO 3
<211> LENGTH: 224
<212> TYPE: PRT
<213> ORGANISM: Homo sapiens

<400> SEQUENCE: 3

```
Met Gly Ser Arg Cys Ala Leu Ala Leu Ala Val Leu Ser Ala Leu Leu
 1               5                  10                  15

Cys Gln Val Trp Ser Ser Gly Val Phe Glu Leu Lys Leu Gln Glu Phe
            20                  25                  30

Val Asn Lys Lys Gly Leu Leu Gly Asn Arg Asn Cys Cys Arg Gly Gly
        35                  40                  45

Ala Gly Pro Pro Cys Ala Cys Arg Thr Phe Phe Arg Val Cys Leu
    50                  55                  60

Lys His Tyr Gln Ala Ser Val Ser Pro Glu Pro Cys Thr Tyr Gly
 65                  70                  75                  80

Ser Ala Val Thr Pro Val Leu Gly Val Asp Ser Phe Ser Leu Pro Asp
                85                  90                  95

Gly Gly Gly Ala Asp Ser Ala Phe Ser Asn Pro Ile Arg Phe Pro Phe
            100                 105                 110

Gly Phe Thr Trp Pro Gly Thr Phe Ser Leu Ile Ile Glu Ala Leu His
        115                 120                 125

Thr Asp Ser Pro Asp Asp Leu Ala Thr Glu Asn Pro Glu Arg Leu Ile
    130                 135                 140

Ser Arg Leu Ala Thr Gln Arg His Leu Thr Val Gly Glu Glu Trp Ser
145                 150                 155                 160

Gln Asp Leu His Ser Ser Gly Arg Thr Asp Leu Lys Tyr Ser Tyr Arg
                165                 170                 175

Phe Val Cys Asp Glu His Tyr Tyr Gly Glu Gly Cys Ser Val Phe Cys
            180                 185                 190

Arg Pro Arg Asp Asp Ala Phe Gly His Phe Thr Cys Gly Glu Arg Gly
        195                 200                 205

Glu Lys Val Cys Asn Pro Gly Trp Lys Gly Pro Tyr Cys Thr Glu Arg
    210                 215                 220
```

<210> SEQ ID NO 4
<211> LENGTH: 203
<212> TYPE: PRT
<213> ORGANISM: Homo sapiens

<400> SEQUENCE: 4

```
Ser Gly Val Phe Glu Leu Lys Leu Gln Glu Phe Val Asn Lys Lys Gly
 1               5                  10                  15

Leu Leu Gly Asn Arg Asn Cys Cys Arg Gly Gly Ala Gly Pro Pro
            20                  25                  30

Cys Ala Cys Arg Thr Phe Phe Arg Val Cys Leu Lys His Tyr Gln Ala
        35                  40                  45
```

```
Ser Val Ser Pro Glu Pro Pro Cys Thr Tyr Gly Ser Ala Val Thr Pro
 50                  55                  60

Val Leu Gly Val Asp Ser Phe Ser Leu Pro Asp Gly Gly Ala Asp
 65              70                  75                  80

Ser Ala Phe Ser Asn Pro Ile Arg Phe Pro Phe Gly Thr Trp Pro
                 85                  90                  95

Gly Thr Phe Ser Leu Ile Ile Glu Ala Leu His Thr Asp Ser Pro Asp
                100                 105                 110

Asp Leu Ala Thr Glu Asn Pro Glu Arg Leu Ile Ser Arg Leu Ala Thr
            115                 120                 125

Gln Arg His Leu Thr Val Gly Glu Trp Ser Gln Asp Leu His Ser
130                 135                 140

Ser Gly Arg Thr Asp Leu Lys Tyr Ser Tyr Arg Phe Val Cys Asp Glu
145                 150                 155                 160

His Tyr Tyr Gly Glu Gly Cys Ser Val Phe Cys Arg Pro Arg Asp Asp
                165                 170                 175

Ala Phe Gly His Phe Thr Cys Gly Glu Arg Gly Glu Lys Val Cys Asn
            180                 185                 190

Pro Gly Trp Lys Gly Pro Tyr Cys Thr Glu Arg
            195                 200

<210> SEQ ID NO 5
<211> LENGTH: 206
<212> TYPE: PRT
<213> ORGANISM: Homo sapiens

<400> SEQUENCE: 5

Val Trp Ser Ser Gly Val Phe Glu Leu Lys Leu Gln Glu Phe Val Asn
 1               5                  10                  15

Lys Lys Gly Leu Leu Gly Asn Arg Asn Cys Cys Arg Gly Gly Ala Gly
                20                  25                  30

Pro Pro Pro Cys Ala Cys Arg Thr Phe Phe Arg Val Cys Leu Lys His
                35                  40                  45

Tyr Gln Ala Ser Val Ser Pro Glu Pro Pro Cys Thr Tyr Gly Ser Ala
 50                  55                  60

Val Thr Pro Val Leu Gly Val Asp Ser Phe Ser Leu Pro Asp Gly Gly
 65                  70                  75                  80

Gly Ala Asp Ser Ala Phe Ser Asn Pro Ile Arg Phe Pro Phe Gly Phe
                 85                  90                  95

Thr Trp Pro Gly Thr Phe Ser Leu Ile Ile Glu Ala Leu His Thr Asp
                100                 105                 110

Ser Pro Asp Asp Leu Ala Thr Glu Asn Pro Glu Arg Leu Ile Ser Arg
            115                 120                 125

Leu Ala Thr Gln Arg His Leu Thr Val Gly Glu Glu Trp Ser Gln Asp
130                 135                 140

Leu His Ser Ser Gly Arg Thr Asp Leu Lys Tyr Ser Tyr Arg Phe Val
145                 150                 155                 160

Cys Asp Glu His Tyr Tyr Gly Glu Gly Cys Ser Val Phe Cys Arg Pro
                165                 170                 175

Arg Asp Asp Ala Phe Gly His Phe Thr Cys Gly Glu Arg Gly Glu Lys
            180                 185                 190

Val Cys Asn Pro Gly Trp Lys Gly Pro Tyr Cys Thr Glu Arg
            195                 200                 205

<210> SEQ ID NO 6
```

<211> LENGTH: 207
<212> TYPE: PRT
<213> ORGANISM: Homo sapiens

<400> SEQUENCE: 6

```
Gln Val Trp Ser Ser Gly Val Phe Glu Leu Lys Leu Gln Glu Phe Val
  1               5                  10                  15

Asn Lys Lys Gly Leu Leu Gly Asn Arg Asn Cys Cys Arg Gly Gly Ala
             20                  25                  30

Gly Pro Pro Pro Cys Ala Cys Arg Thr Phe Phe Arg Val Cys Leu Lys
         35                  40                  45

His Tyr Gln Ala Ser Val Ser Pro Glu Pro Pro Cys Thr Tyr Gly Ser
     50                  55                  60

Ala Val Thr Pro Val Leu Gly Val Asp Ser Phe Ser Leu Pro Asp Gly
 65                  70                  75                  80

Gly Gly Ala Asp Ser Ala Phe Ser Asn Pro Ile Arg Phe Pro Phe Gly
                 85                  90                  95

Phe Thr Trp Pro Gly Thr Phe Ser Leu Ile Ile Glu Ala Leu His Thr
            100                 105                 110

Asp Ser Pro Asp Asp Leu Ala Thr Glu Asn Pro Glu Arg Leu Ile Ser
        115                 120                 125

Arg Leu Ala Thr Gln Arg His Leu Thr Val Gly Glu Glu Trp Ser Gln
130                 135                 140

Asp Leu His Ser Ser Gly Arg Thr Asp Leu Lys Tyr Ser Tyr Arg Phe
145                 150                 155                 160

Val Cys Asp Glu His Tyr Tyr Gly Glu Gly Cys Ser Val Phe Cys Arg
                165                 170                 175

Pro Arg Asp Asp Ala Phe Gly His Phe Thr Cys Gly Glu Arg Gly Glu
            180                 185                 190

Lys Val Cys Asn Pro Gly Trp Lys Gly Pro Tyr Cys Thr Glu Arg
        195                 200                 205
```

<210> SEQ ID NO 7
<211> LENGTH: 723
<212> TYPE: PRT
<213> ORGANISM: Homo sapiens

<400> SEQUENCE: 7

```
Met Gly Ser Arg Cys Ala Leu Ala Leu Ala Val Leu Ser Ala Leu Leu
  1               5                  10                  15

Cys Gln Val Trp Ser Ser Gly Val Phe Glu Leu Lys Leu Gln Glu Phe
             20                  25                  30

Val Asn Lys Lys Gly Leu Leu Gly Asn Arg Asn Cys Cys Arg Gly Gly
         35                  40                  45

Ala Gly Pro Pro Pro Cys Ala Cys Arg Thr Phe Phe Arg Val Cys Leu
     50                  55                  60

Lys His Tyr Gln Ala Ser Val Ser Pro Glu Pro Pro Cys Thr Tyr Gly
 65                  70                  75                  80

Ser Ala Val Thr Pro Val Leu Gly Val Asp Ser Phe Ser Leu Pro Asp
                 85                  90                  95

Gly Gly Gly Ala Asp Ser Ala Phe Ser Asn Pro Ile Arg Phe Pro Phe
            100                 105                 110

Gly Phe Thr Trp Pro Gly Thr Phe Ser Leu Ile Ile Glu Ala Leu His
        115                 120                 125

Thr Asp Ser Pro Asp Asp Leu Ala Thr Glu Asn Pro Glu Arg Leu Ile
130                 135                 140
```

```
Ser Arg Leu Ala Thr Gln Arg His Leu Thr Val Gly Glu Glu Trp Ser
145                 150                 155                 160

Gln Asp Leu His Ser Ser Gly Arg Thr Asp Leu Lys Tyr Ser Tyr Arg
            165                 170                 175

Phe Val Cys Asp Glu His Tyr Tyr Gly Glu Gly Cys Ser Val Phe Cys
            180                 185                 190

Arg Pro Arg Asp Asp Ala Phe Gly His Phe Thr Cys Gly Glu Arg Gly
            195                 200                 205

Glu Lys Val Cys Asn Pro Gly Trp Lys Gly Pro Tyr Cys Thr Glu Pro
210                 215                 220

Ile Cys Leu Pro Gly Cys Asp Glu Gln His Gly Phe Cys Asp Lys Pro
225                 230                 235                 240

Gly Glu Cys Lys Cys Arg Val Gly Trp Gln Gly Arg Tyr Cys Asp Glu
            245                 250                 255

Cys Ile Arg Tyr Pro Gly Cys Leu His Gly Thr Cys Gln Gln Pro Trp
            260                 265                 270

Gln Cys Asn Cys Gln Glu Gly Trp Gly Gly Leu Phe Cys Asn Gln Asp
            275                 280                 285

Leu Asn Tyr Cys Thr His His Lys Pro Cys Lys Asn Gly Ala Thr Cys
290                 295                 300

Thr Asn Thr Gly Gln Gly Ser Tyr Thr Cys Ser Cys Arg Pro Gly Tyr
305                 310                 315                 320

Thr Gly Ala Thr Cys Glu Leu Gly Ile Asp Glu Cys Asp Pro Ser Pro
            325                 330                 335

Cys Lys Asn Gly Gly Ser Cys Thr Asp Leu Glu Asn Ser Tyr Ser Cys
            340                 345                 350

Thr Cys Pro Pro Gly Phe Tyr Gly Lys Ile Cys Glu Leu Ser Ala Met
            355                 360                 365

Thr Cys Ala Asp Gly Pro Cys Phe Asn Gly Gly Arg Cys Ser Asp Ser
            370                 375                 380

Pro Asp Gly Gly Tyr Ser Cys Arg Cys Pro Val Gly Tyr Ser Gly Phe
385                 390                 395                 400

Asn Cys Glu Lys Lys Ile Asp Tyr Cys Ser Ser Pro Cys Ser Asn
            405                 410                 415

Gly Ala Lys Cys Val Asp Leu Gly Asp Ala Tyr Leu Cys Arg Cys Gln
            420                 425                 430

Ala Gly Phe Ser Gly Arg His Cys Asp Asp Asn Val Asp Asp Cys Ala
            435                 440                 445

Ser Ser Pro Cys Ala Asn Gly Gly Thr Cys Arg Asp Gly Val Asn Asp
450                 455                 460

Phe Ser Cys Thr Cys Pro Pro Gly Tyr Thr Gly Arg Asn Cys Ser Ala
465                 470                 475                 480

Pro Val Ser Arg Cys Glu His Ala Pro Cys His Asn Gly Ala Thr Cys
            485                 490                 495

His Gln Arg Gly His Gly Tyr Val Cys Glu Cys Ala Arg Ser Tyr Gly
            500                 505                 510

Gly Pro Asn Cys Gln Phe Leu Leu Pro Glu Leu Pro Gly Pro Ala
            515                 520                 525

Val Val Asp Leu Thr Glu Lys Leu Glu Gly Gln Gly Gly Pro Phe Pro
            530                 535                 540

Trp Val Ala Val Cys Ala Gly Val Ile Leu Val Leu Met Leu Leu Leu
545                 550                 555                 560
```

```
Gly Cys Ala Ala Val Val Cys Val Arg Leu Arg Leu Gln Lys His
                565                 570                 575
Arg Pro Pro Ala Asp Pro Cys Arg Gly Glu Thr Glu Thr Met Asn Asn
            580                 585                 590
Leu Ala Asn Cys Gln Arg Glu Lys Asp Ile Ser Val Ser Ile Ile Gly
        595                 600                 605
Ala Thr Gln Ile Lys Asn Thr Asn Lys Lys Ala Asp Phe His Gly Asp
    610                 615                 620
His Ser Ala Asp Lys Asn Gly Phe Lys Ala Arg Tyr Pro Ala Val Asp
625                 630                 635                 640
Tyr Asn Leu Val Gln Asp Leu Lys Gly Asp Thr Ala Val Arg Asp
                645                 650                 655
Ala His Ser Lys Arg Asp Thr Lys Cys Gln Pro Gln Gly Ser Ser Gly
                660                 665                 670
Glu Glu Lys Gly Thr Pro Thr Thr Leu Arg Gly Gly Glu Ala Ser Glu
            675                 680                 685
Arg Lys Arg Pro Asp Ser Gly Cys Ser Thr Ser Lys Asp Thr Lys Tyr
        690                 695                 700
Gln Ser Val Tyr Val Ile Ser Glu Glu Lys Asp Glu Cys Val Ile Ala
705                 710                 715                 720
Thr Glu Val

<210> SEQ ID NO 8
<211> LENGTH: 2303
<212> TYPE: DNA
<213> ORGANISM: Homo sapiens

<400> SEQUENCE: 8
atgggcagtc ggtgcgcgct ggccctggcg gtgctctcgg ccttgctgtg tcaggtctgg      60
agctctgggg tgttcgaact gaagctgcag gagttcgtca acaagaaggg gctgctgggg     120
aaccgcaact gctgccgcgg gggcgcgggg ccaccgccgt gcgcctgccg gaccttcttc     180
cgcgtgtgcc tcaagcacta ccaggccagc gtgtccccg agccgccctg cacctacggc     240
agcgccgtca ccccgtgct gggcgtcgac tccttcagtc tgcccgacgg cggggcgcc      300 gactccgcgt tcagcaaccc catccgcttc cccttcggct tcacctggcc gggcaccttc     360
tctctgatta ttgaagctct ccacacagat tctcctgatg acctcgcaac agaaaaccca     420
gaaagactca tcagccgcct ggccacccag aggcacctga cggtgggcga ggagtggtcc     480
caggacctgc acagcagcgg ccgcacggac ctcaagtact cctaccgctt cgtgtgtgac     540
gaacactact acggagaggg ctgctccgtt ttctgccgtc cccgggacga tgccttcggc     600
cacttcacct gtggggagcg tggggagaaa gtgtgcaacc tggctggaa agggccctac     660 tgcacagagc ggtagccaga aacttaaact ttttttcttca aacactgaag tctctcccg     720 cccccagctc gcgcgtgcca tagattagat ctctccgggg ataggcgcag gacacccgc     780 cggctcccat tggcggaagg gcgatctgcc tgcctggatg tgatgagcag catggatttt     840
gtgacaaacc aggggaatgc aagtgcagag tgggctggca gggccggtac tgtgacgagt     900
gtatccgcta tccaggctgt ctccatggca cctgccagca gccctggcag tgcaactgcc     960
aggaaggctg ggggggcctt ttctgcaacc aggacctgaa ctactgcaca ccataagc     1020 cctgcaagaa tggagccacc tgcaccaaca cgggcagggg agctacact tgctcttgcc    1080 ggcctgggta cacaggtgcc acctgcgagc tggggattga cgagtgtgac ccagccctt    1140 gtaagaacgg agggagctgc acggatctcg agaacagcta ctcctgtacc tgcccacccg    1200
```

```
gcttctacgg caaaatctgt gaattgagtg ccatgacctg tgcggacggc ccttgcttta    1260 acggggtcg gtgctcagac agccccgatg gagggtacag ctgccgctgc ccgtgggct     1320 actccggctt caactgtgag aagaaaattg actactgcag ctcttcaccc tgttctaatg   1380
gtgccaagtg tgtggacctc ggtgatgcct acctgtgccg ctgccaggcc ggcttctcgg   1440
ggaggcactg tgacgacaac gtggacgact gcgcctcctc ccgtgcgcc aacgggggca    1500 cctgccggga tggcgtgaac gacttctcct gcacctgccc gcctggctac acgggcagga   1560
actgcagtgc ccccgtcagc aggtgcgagc acgcaccctg ccacaatggg gccacctgcc   1620
accagagggg ccacggctat gtgtgcgaat gtgcccgaag ctacggggt cccaactgcc    1680 agttcctgct ccccgagctg ccccggggc cagcggtggt ggacctcact gagaagctag    1740
agggccaggg cgggccattc ccctgggtgg ccgtgtgcgc cggggtcatc cttgtcctca   1800
tgctgctgct gggctgtgcc gctgtggtgg tctgcgtccg gctgaggctg cagaagcacc   1860 ggccccccagc cgacccctgc cggggggaga cggagaccat gaacaacctg ccaactgcc   1920 agcgtgagaa ggacatctca gtcagcatca tcggggccac gcagatcaag aacaccaaca   1980
agaaggcgga cttccacggg gaccacagcg ccgacaagaa tggcttcaag gcccgctacc   2040
cagcggtgga ctataacctc gtgcaggacc tcaaggtgac gacaccgcc gtcagggacg    2100 cgcacagcaa gcgtgacacc aagtgccagc ccagggctc ctcaggggag gagaagggaa    2160
ccccgaccac actcagggt ggagaagcat ctgaaagaaa aaggccggac tcgggctgtt    2220
caacttcaaa agacaccaag taccagtcgg tgtacgtcat atccgaggag aaggatgagt   2280
gcgtcatagc aactgaggtg taa                                           2303

<210> SEQ ID NO 9
<211> LENGTH: 2988
<212> TYPE: DNA
<213> ORGANISM: Homo sapiens

<400> SEQUENCE: 9
aaaccggaac ggggcccaac ttctgggggcc tggagaaggg aaacgaagtc ccccccggtt    60
tcccgaggtt gcctttcctc gggcatcctt ggtttcggcg ggacttcgca gggcggatat   120
aaagaacggc gcctttggga agaggcggag accggcttta agaaagaag tcttggtcct    180 gcggcttggg cgaggcaagg gcgaggcaag ggcgctttct gccgacgctc cccgtggccc   240
tacgatcccc cgcgcgtccg ccgctgttct aaggagagaa gtgggggccc ccaggctcg    300 cgcgtggagc gaagcagcat ggcagtcgg tgcgcgctgg ccctggcggt gctctcggcc   360
ttgctgtgtc aggtctggag ctctgggggtg ttcgaactga gctgcagga gttcgtcaac   420 aagaagggc tgctggggaa ccgcaactgc tgccgcgggg gcgcggggcc accgccgtgc    480
gcctgccgga ccttcttccg cgtgtgcctc aagcactacc aggccagcgt gtcccccgag   540
ccgccctgca cctacggcag cgccgtcacc cccgtgctgg gcgtcgactc cttcagtctg   600
cccgacggcg ggggcgccga ctccgcgttc agcaaccca tccgcttccc cttcggcttc   660
acctggccgg gcaccttctc tctgattatt gaagctctcc acacagattc tcctgatgac   720
ctcgcaacag aaaacccaga aagactcatc agccgcctgg ccacccagag gcacctgacg   780
gtgggcgagg agtggtccca ggacctgcac agcagcggcc gcacggacct caagtactcc   840
taccgcttcg tgtgtgacga acactactac ggagagggct gctccgtttt ctgccgtccc   900
cgggacgatg ccttcggcca cttcacctgt ggggagcgtg gggagaaagt gtgcaaccct   960
```

```
ggctggaaag ggccctactg cacagagccg atctgcctgc ctggatgtga tgagcagcat   1020
ggattttgtg acaaaccagg ggaatgcaag tgcagagtgg gctggcaggg ccggtactgt   1080
gacgagtgta ccgctatcc aggctgtctc catggcacct gccagcagcc ctggcagtgc    1140
aactgccagg aaggctgggg gggccttttc tgcaaccagg acctgaacta ctgcacacac   1200
cataagccct gcaagaatgg agccacctgc accaacacgg gccaggggag ctacacttgc   1260
tcttgccggc ctgggtacac aggtgccacc tgcgagctgg ggattgacga gtgtgacccc   1320
agcccttgta gaacggagg gagctgcacg atctcgaga acagctactc ctgtacctgc    1380
ccacccggct tctacggcaa aatctgtgaa ttgagtgcca tgacctgtgc ggacggccct   1440
tgctttaacg ggggtcggtg ctcagacagc cccgatggag ggtacagctg ccgctgcccc   1500
gtgggctact ccggcttcaa ctgtgagaag aaaattgact actgcagctc ttcaccctgt   1560
tctaatggtg ccaagtgtgt ggacctcggt gatgcctacc tgtgccgctg ccaggccggc   1620
ttctcgggga ggcactgtga cgacaacgtg gacgactgcg cctcctcccc gtgcgccaac   1680
gggggcacct gccgggatgg cgtgaacgac ttctcctgca cctgcccgcc tggctacacg   1740
ggcaggaact gcagtgcccc cgtcagcagg tgcgagcacg cccctgcca caatggggcc    1800 acctgccacc agaggggcca cggctatgtg tgcgaatgtg cccgaagcta cggggggtccc   1860 aactgccagt cctgctcccc cgagctgccc cggggcccag cggtggtgga cctcactgag   1920
aagctagagg gccagggcgg gccattcccc tgggtggccg tgtgcgccgg ggtcatcctt   1980
gtcctcatgc tgctgctggg ctgtgccgct gtggtggtct cgtccggct gaggctgcag    2040 aagcaccggc ccccagccga ccccttgccgg ggggagacgg agaccatgaa caacctggcc   2100
aactgccagc gtgagaagga catctcagtc agcatcatcg gggccacgca gatcaagaac   2160
accaacaaga aggcggactt ccacggggac acagcgccg acaagaatgg cttcaaggcc    2220
cgctacccag cggtggacta aaccctcgtg caggacctca agggtgacga caccgccgtc   2280
agggacgcgc acagcaagcg tgacaccaag tgccagcccc agggctcctc aggggaggag   2340
aaggggaccc cgaccacact caggggtgga gaagcatctg aaagaaaaag gccggactcg   2400
ggctgttcaa cttcaaaaga caccaagtac cagtcggtgt acgtcatatc cgaggagaag   2460
gatgagtgcg tcatagcaac tgaggtgtaa aatggaagtg agatggcaag actcccgttt   2520
ctcttaaaat aagtaaaatt ccaaggatat atgccccaac gaatgctgct gaagaggagg   2580
gaggcctcgt ggactgctgc tgagaaaccg agttcagacc gagcaggttc tcctcctgag   2640
gtcctcgacg cctgccgaca gcctgtcgcg gcccggccgc ctgcggcact gccttccgtg   2700
acgtcgccgt tgcactatgg acagttgctc ttaagagaat atatatttaa atgggtgaac   2760
tgaattacgc ctaagaagca tgcactgcct gagtgtatat tttggattct tatgagccag   2820
tcttttcttg aattagaaac acaaacactg cctttattgt ccttttttgat acgaagatgt   2880 gcttttctta gatggaaaag atgtgtgtta tttttttggat ttgtaaaaat attttttcatg   2940 atatctgtaa agcttgagta ttttgtgatg ttcgtttttt ataattta              2988
```

<210> SEQ ID NO 10  
<211> LENGTH: 3158  
<212> TYPE: DNA  
<213> ORGANISM: Homo sapiens

<400> SEQUENCE: 10

```
aaaccggaac gggccccaac ttctgggggcc tggagaaggg aaacgaagtc cccccccggtt   60 tcccgaggtt gcctttcctc gggcatcctt ggtttcggcg ggacttcgca gggcggatat   120
```

```
aaagaacggc gcctttggga agaggcggag accggcttta aagaaagaag tcttggtcct    180
gcggcttggg cgaggcaagg gcgaggcaag ggcgctttct gccgacgctc cccgtggccc    240
tacgatcccc cgcgcgtccg ccgctgttct aaggagagaa gtgggggccc cccaggctcg    300
cgcgtggagc gaagcagcat gggcagtcgg tgcgcgctgg ccctggcggt gctctcggcc    360
ttgctgtgtc aggtctggag ctctggggtg ttcgaactga agctgcagga gttcgtcaac    420 aagaagggc tgctggggaa ccgcaactgc tgccgcgggg gcgcggggcc accgccgtgc     480
gcctgccgga ccttcttccg cgtgtgcctc aagcactacc aggccagcgt gtcccccgag    540
ccgccctgca cctacggcag cgccgtcacc cccgtgctgg gcgtcgactc cttcagtctg    600
cccgacggcg gggcgccga ctccgcgttc agcaaccca tccgcttccc cttcggcttc      660
acctggccgg gcaccttctc tctgattatt gaagctctcc acacagattc tcctgatgac    720
ctcgcaacag aaaacccaga aagactcatc agccgcctgg ccaccagag gcacctgacg     780 gtgggcgagg agtggtccca ggacctgcac agcagcggcc gcacggacct caagtactcc    840
taccgcttcg tgtgtgacga acactactac ggagagggct gctccgtttt ctgccgtccc    900
cgggacgatg ccttcggcca cttcacctgt ggggagcgtg gggagaaagt gtgcaaccct    960
ggctggaaag ggccctactg cacagagccg atctgcctgc ctggatgtga tgagcagcat   1020
ggattttgtg acaaaccagg ggaatgcaag tgcagagtgg gctggcaggg ccggtactgt   1080
gacgagtgta tccgctatcc aggctgtctc catggcacct gccagcagcc ctggcagtgc   1140
aactgccaga aggctgggg gggccttttc tgcaaccagg acctgaacta ctgcacacac    1200
cataagccct gcaagaatgg agccacctgc accaacacgg gccaggggag ctacacttgc   1260
tcttgccggc ctgggtacac aggtgccacc tgcgagctgg ggattgacga gtgtgacccc   1320
agcccttgta agaacggagg gagctgcacg gatctcgaga acagctactc ctgtacctgc   1380
ccacccggct tctacggcaa aatctgtgaa ttgagtgcca tgacctgtgc ggacggccct   1440
tgctttaacg ggggtcggtg ctcagacagc cccgatggag ggtacagctg ccgctgcccc   1500
gtgggctact ccggcttcaa ctgtgagaag aaaattgact actgcagctc ttcaccctgt   1560
tctaatggtg ccaagtgtgt ggacctcggt gatgcctacc tgtgccgctg ccaggccggc   1620
ttctcgggga ggcactgtga cgacaacgtg gacgactgcg cctcctcccc gtgcgccaac   1680 ggggcacct gccgggatgg cgtgaacgac ttctcctgca cctgcccgcc tggctacacg    1740
ggcaggaact gcagtgcccc cgtcagcagg tgcgagcacg cccctgcca caatggggcc    1800 acctgccacc agaggggcca cggctatgtg tgcgaatgtg cccgaagcta cggggtccc    1860 aactgccagt tcctgctccc cgagctgccc cggggcccag cggtggtgga cctcactgag   1920
aagctagagg gccagggcgg gccattcccc tgggtggccg tgtgcgccgg ggtcatcctt   1980
gtcctcatgc tgctgctggg ctgtgccgct gtggtggtct cgtccggct gaggctgcag   2040 aagcaccggc ccccagccga cccctgccgg ggggagacgg agaccatgaa caacctggcc   2100
aactgccagc gtgagaagga catctcagtc agcatcatcg gggccacgca gatcaagaac   2160
accaacaaga aggcggactt ccacggggac acagcgccg acaagaatgg cttcaaggcc    2220
cgctacccag cggtggacta taacctcgtg caggacctca agggtgacga caccgccgtc   2280
agggacgcgc acagcaagcg tgacaccaag tgccagcccc agggctcctc aggggaggag   2340
aaggggaccc cgaccacact cagggtgga aagcatctg aaagaaaaag gccggactcg     2400
ggctgttcaa cttcaaaaga caccaagtac cagtcggtgt acgtcatatc cgaggagaag   2460
```

```
gatgagtgcg tcatagcaac tgaggtgtaa aatggaagtg agatggcaag actcccgttt    2520
ctcttaaaat aagtaaaatt ccaaggatat atgccccaac gaatgctgct gaagaggagg    2580
gaggcctcgt ggactgctgc tgagaaaccg agttcagacc gagcaggttc tcctcctgag    2640
gtcctcgacg cctgccgaca gcctgtcgcg gcccggccgc ctgcggcact gccttccgtg    2700
acgtcgccgt tgcactatgg acagttgctc ttaagagaat atatatttaa atgggtgaac    2760
tgaattacgc taagaagca tgcactgcct gagtgtatat tttggattct tatgagccag     2820
tcttttcttg aattagaaac acaaacactg cctttattgt cctttttgat acgaagatgt    2880 gcttttcta gatggaaaag atgtgtgtta ttttttggat tgtaaaaat attttttcatg     2940 atatctgtaa agcttgagta ttttgtgatg ttcgtttttt ataatttaaa ttttggtaaa    3000
tatgtacaaa ggcacttcgg gtctatgtga ctatattttt ttgtatataa atgtatttat    3060
ggaatattgt gccaatgtta tttgagtttt ttactgtttt gttaatgaag aaattccttt    3120
ttaaaatatt tttccaaaat aaattttatg aggaattc                            3158

<210> SEQ ID NO 11
<211> LENGTH: 684
<212> TYPE: DNA
<213> ORGANISM: Homo sapiens
<220> FEATURE:
<221> NAME/KEY: modified_base
<222> LOCATION: (1)..(83)
<223> OTHER INFORMATION: a, c, g, t, unknown, or other

<400> SEQUENCE: 11
nnnnnnnnnn nnnnnnnnnn nnnnnnnnnn nnnnnnnnnn nnnnnnnnnn nnnnnnnnnn      60
nnnnnnnnnn nnnnnnnnnn nnngaggagg gaggcctcgt ggactgctgc tgagaaaccg     120
agttcagacc gagcaggttc tcctcctgag gtcctcgacg cctgccgaca gcctgtcgcg     180
gcccggccgc ctgcggcact gccttccgtg acgtcgccgt tgcactatgg acagttgctc     240
ttaagagaat atatatttaa atgggtgaac tgaattacgc ataagaagca tgcactgcct     300
gagtgtatat tttggattct tatgagccag tcttttcttg aattagaaac acaaacactg     360
cctttattgt cctttttgat acgaagatgt gcttttcta gatggaaaag atgtgtgtta     420
ttttttggat tgtaaaaat attttttcatg atatctgtaa agcttgagta ttttgtgatg     480
ttcgtttttt ataatttaaa ttttggtaaa tatgtacaaa ggcacttcgg gtctatgtga     540
ctatattttt ttgtatataa atgtatttat ggaatattgt gcaaatgtta tttgagtttt    600
ttactgtttt gttaatgaag aaattccttt ttaaaatatt tttcgcaaaa taaattttat    660
gaatgacaaa aaaaaaaaa aaaa                                             684

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
caccatgggc agtcggtgcg cgctgg                                           26

<210> SEQ ID NO 13
<211> LENGTH: 28
<212> TYPE: DNA
<213> ORGANISM: Artificial Sequence
<220> FEATURE:
```

-continued

```
<223> OTHER INFORMATION: Description of Artificial Sequence: Synthetic
      primer

<400> SEQUENCE: 13
ctaccgctct gtgcagtagg gccctttc                                              28

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 14

His His His His His His
  1               5
```